United States Patent
Hynes et al.

(10) Patent No.: US 9,549,723 B2
(45) Date of Patent: Jan. 24, 2017

(54) SURGICAL INSTRUMENTATION AND METHOD

(71) Applicant: Warsaw Orthopedic, Inc., Warsaw, IN (US)

(72) Inventors: Richard A. Hynes, Melbourne Beach, FL (US); Anthony J. Melkent, Germantown, TN (US); Stanley T. Palmatier, Olive Branch, MS (US)

(73) Assignee: Warsaw Othropedic, Inc., Warsaw, IN (US)

( * ) Notice: Subject to any disclaimer, the term of this patent is extended or adjusted under 35 U.S.C. 154(b) by 84 days.

(21) Appl. No.: 14/219,821

(22) Filed: Mar. 19, 2014

(65) Prior Publication Data

US 2015/0265265 A1    Sep. 24, 2015

(51) Int. Cl.
*A61B 17/02* (2006.01)
*A61B 17/28* (2006.01)
*A61B 17/00* (2006.01)

(52) U.S. Cl.
CPC ............. *A61B 17/025* (2013.01); *A61B 17/02* (2013.01); *A61B 90/30* (2016.02); *A61B 17/0293* (2013.01); *A61B 17/2833* (2013.01); *A61B 2017/00477* (2013.01); *A61B 2017/0256* (2013.01); *A61B 2017/2837* (2013.01)

(58) Field of Classification Search
CPC .................................................. A61B 17/025
See application file for complete search history.

(56) References Cited

U.S. PATENT DOCUMENTS

| 1,706,500 | A | 3/1929 | Smith |
| 5,928,139 | A * | 7/1999 | Koros ................ A61B 17/0206 600/205 |
| 7,594,888 | B2 * | 9/2009 | Raymond .......... A61B 17/3439 600/215 |
| 7,618,431 | B2 | 11/2009 | Roehm, III |
| 7,981,029 | B2 | 7/2011 | Branch et al. |
| 8,000,782 | B2 | 8/2011 | Gharib et al. |
| 8,005,535 | B2 | 8/2011 | Gharib et al. |
| 8,016,767 | B2 | 9/2011 | Miles et al. |
| 8,062,217 | B2 * | 11/2011 | Boucher ............ A61B 17/0206 600/215 |
| 8,192,356 | B2 | 6/2012 | Miles et al. |
| 2004/0176665 | A1 * | 9/2004 | Branch .............. A61B 17/0206 600/210 |
| 2006/0106416 | A1 * | 5/2006 | Raymond .............. A61B 17/02 606/198 |

(Continued)

FOREIGN PATENT DOCUMENTS

EP    0951868 A1    10/1999

*Primary Examiner* — Ellen C Hammond

(57) ABSTRACT

A surgical instrument includes a first member having an inner surface and an outer surface. A second member has an inner surface and an outer surface. At least one of the inner surfaces defines at least one mating element and the outer surfaces are engageable with tissue. The members are relatively movable between a first configuration and a second configuration to space the tissue and define an opening between the members. At least one third member defines at least one mating element engageable with the at least one mating element of the inner surface such that the at least one third member is disposed within the opening. Systems and methods are disclosed.

20 Claims, 26 Drawing Sheets

(56) References Cited

U.S. PATENT DOCUMENTS

| | | | | |
|---|---|---|---|---|
| 2006/0142643 A1* | 6/2006 | Parker | ................... | A61B 1/32 |
| | | | | 600/219 |
| 2007/0293729 A1* | 12/2007 | Grey | ................. | A61B 1/00105 |
| | | | | 600/212 |
| 2008/0183046 A1* | 7/2008 | Boucher | ............ | A61B 17/0206 |
| | | | | 600/232 |

* cited by examiner

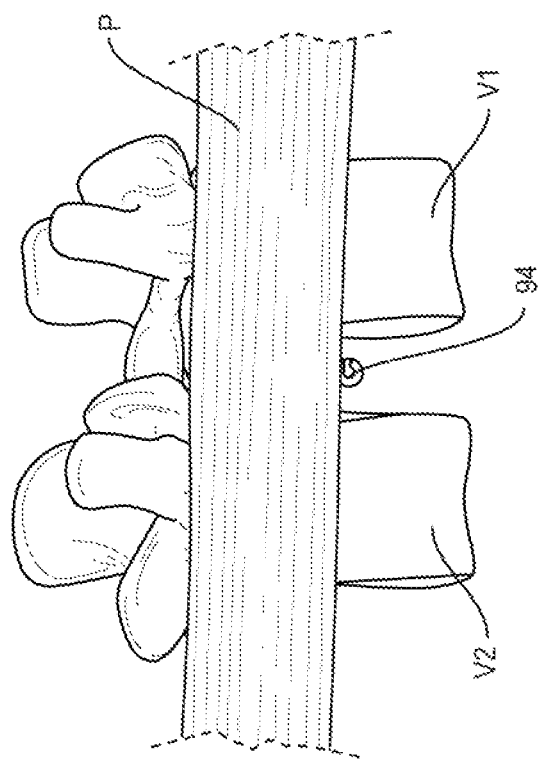

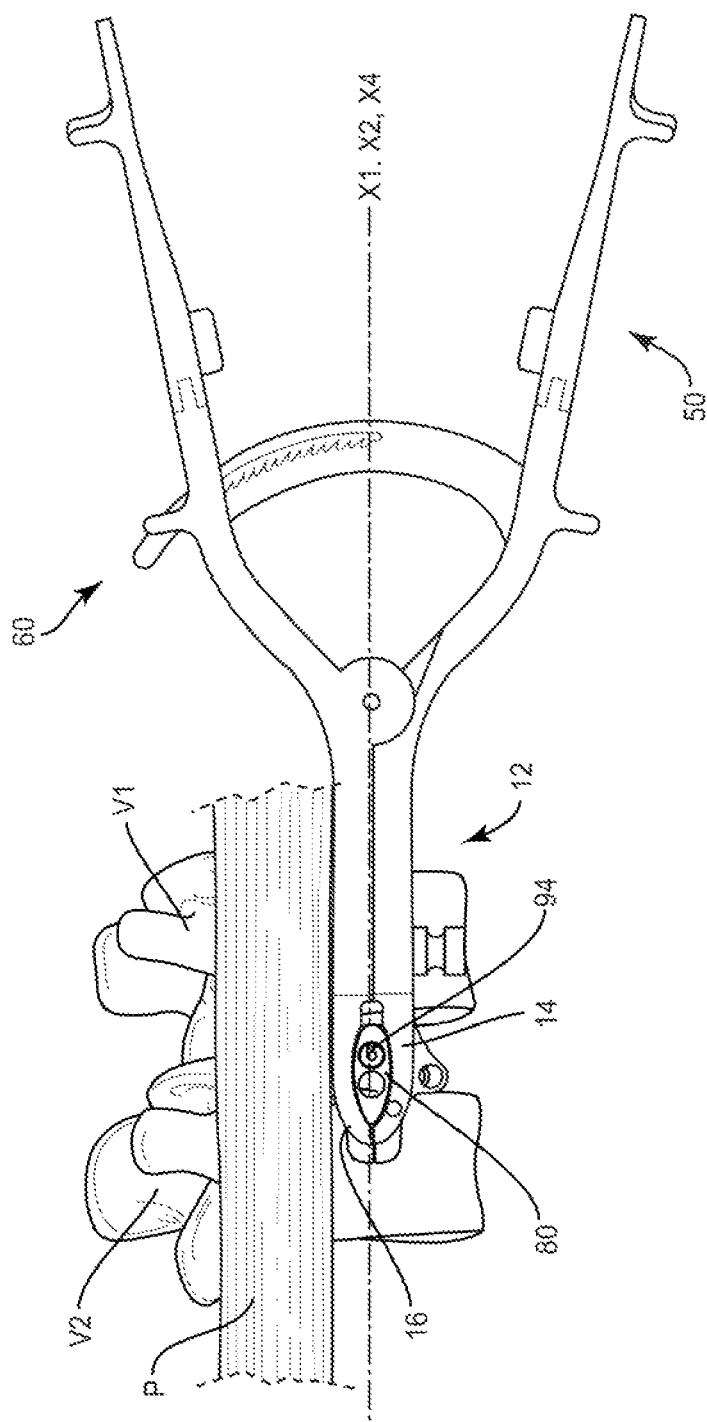

SURGICAL INSTRUMENTATION AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondyolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discetomy, laminectomy, corpectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Certain spinal surgery approaches utilize a direct lateral approach to access lumbar disc spaces, however, these techniques present certain challenges due to the location of musculature and neural structures embedded therein.

This disclosure describes an improvement over these prior art technologies with the provision of specialized instrumentation, implants and techniques to allow for a surgical pathway to the lumbar disc spaces.

SUMMARY

Systems and methods of use for accessing disc spaces are provided. In some embodiments, a surgical instrument is provided. The surgical instrument includes a first member having an inner surface and an outer surface. A second member has an inner surface and an outer surface. At least one of the inner surfaces defines at least one mating element and the outer surfaces are engageable with tissue. The members are relatively movable between a first configuration and a second configuration to space the tissue and define an opening between the members. At least one third member defines at least one mating element engageable with the at least one mating element of the inner surface such that the at least one third member is disposed within the opening.

BRIEF DESCRIPTION OF THE DRAWINGS

The present disclosure will become more readily apparent from the specific description accompanied by the following drawings, in which:

FIG. 6 is a side view of the component and vertebrae shown in FIG. 4;

FIG. 16 is a side view of the components and vertebrae shown in FIG. 15;

DETAILED DESCRIPTION

Figure 1:
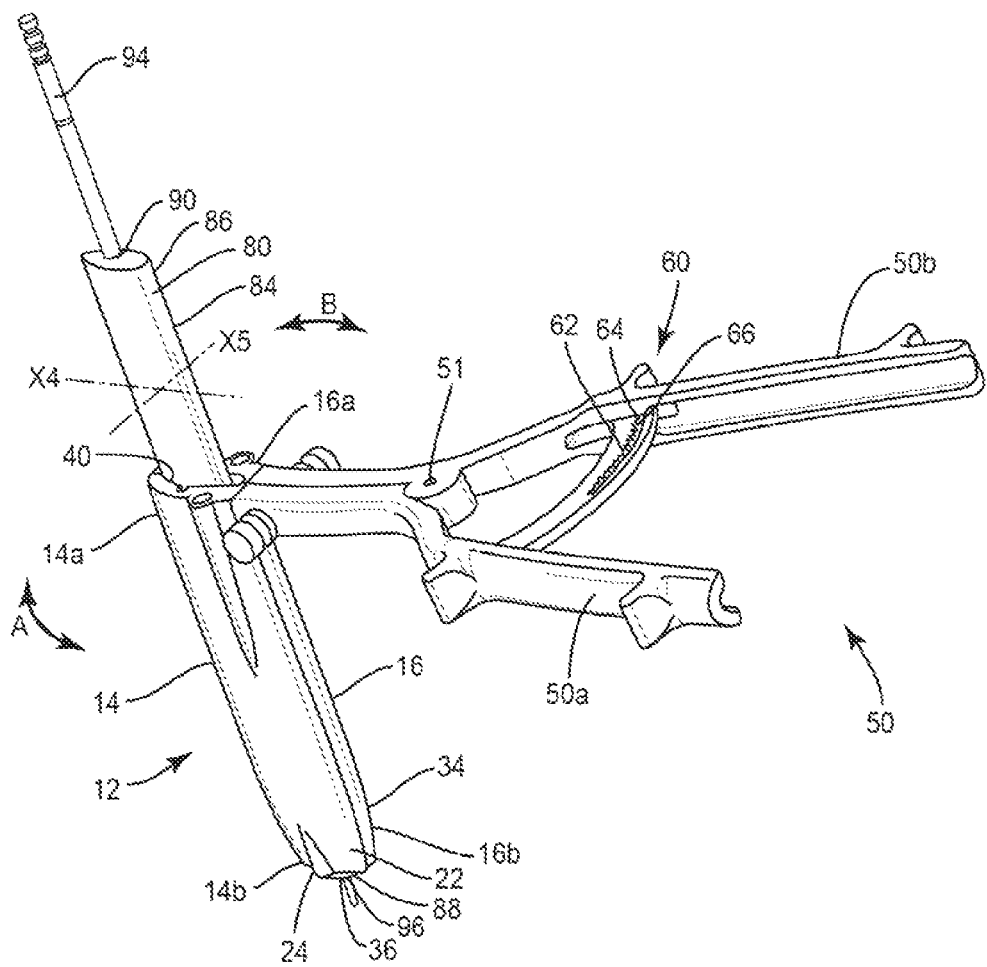
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In one embodiment, the systems and methods of the present disclosure are employed with a spinal joint and fusion, for example, with a cervical, thoracic, lumbar and/or sacral region of a spine.

In one embodiment, the surgical system includes a surgical instrument, such as, for example, a retractor having interlocking blades. In some embodiments, the retractor includes retractor blades and one or a plurality of interlocking blades attachable therewith. In some embodiments, the retractor blades include one or more grooves such that an interlocking blade can be translated to close and/or partially close a gap of the retractor blades. In some embodiments, an anterior portion of the retractor blades includes a groove such that an interlocking blade is slid along the groove and into position to close an anterior gap between the retractor blades. In some embodiments, a posterior portion of the retractor blades includes a groove such that an interlocking blade is slid along the groove and into position to close a posterior gap between the retractor blades.

In some embodiments, the retractor can include interlocking and/or interleaved blades, for example, in a three blade embodiment that partially encloses a surgical pathway and/or corridor, and for example, in a four blade embodiment that fully encloses a surgical pathway and/or corridor. In some embodiments, the retractor can include one or a plurality of interlocking wedges that connect with the retractor blades. In some embodiments, the interlocking wedges connect with the retractor blades in a dovetail connection. In some embodiments, the retractor includes a blade having a pin hole on a superior blade disposed adjacent an edge surface. In some embodiments, the retractor can include interlocking blades having a variety of widths to accommodate different retractor openings.

In one embodiment, the surgical system is employed with a method including an oblique lateral interbody fusion (OLIF) procedure in the lower lumbar region between an L1 vertebral body and an L5 vertebral body using an anterolateral operative corridor between a posterior psoas muscle and an anterior vasculature, such as, for example, the vena cava and aorta. In one embodiment, the patient is placed on their side, left side up, to position the vena cava on the right side of a centerline. In one embodiment, the surgical system displaces the psoas muscle posteriorly thereby avoiding teasing apart the muscle fibers and disrupting nerves located in the psoas muscle in the L1-L5 vertebral region. In one embodiment, the psoas muscle is numbed and/or paralyzed during the surgical procedure.

In one embodiment, the surgical system includes a surgical instrument such as, for example, a retractor configured for use with an OLIF procedure for treating the L2-L5 vertebral region. In one embodiment, the surgical system includes non-modular components and/or attachments. In one embodiment, the retractor includes relatively flat blades to allow for plate and screw placement and blade pin placement away from a center of body/segmental vessels. In one embodiment, the retractor includes stiff and biased blades. In one embodiment, the retractor includes blades having an oval blade shape, which facilitates lateral sweeping of the psoas muscle. In one embodiment, the lateral sweeping can include rotating the blades and/or the oval shaped blade dilator to move the psoas muscle. In one embodiment, the retractor includes a light for visualization of a surgical site.

In one embodiment, the system includes a retractor having a tapered portion to facilitate insertion and displacement of psoas tissue. In one embodiment, the retractor blades include a lip on an end of the retractor blade. In one embodiment, the lip is configured to be rotated under the psoas muscle after the blades are positioned adjacent to the spine. This configuration prevents the psoas muscle from creeping under the blades.

In one embodiment, the system includes an oval dilator having offset passageways to facilitate final positioning of the retractor in an anterior or posterior orientation relative to an initial dilator. In one embodiment, an end portion of the retractor blades and/or the oval dilator are concave to facilitate positioning against and/or conforming to a vertebral body.

In one embodiment, the retractor blades are connected with a handle. In one embodiment, the handle is connected at an angle to the retractor blades so that handles do not interfere with an iliac crest. In one embodiment, an angled handle connection is configured to force tips of the retractor blades to diverge when opened such that the tips counteract tissues forces that would normally bias the retractor blades to a closed position. The retractor blades can be configured for internal rotation when closed such that when they are opened, they are approximately parallel.

In one embodiment, an initial dilator tip is integrated into the oval dilator thereby eliminating the initial dilator step. In some embodiments, the initial dilator tip can be disposed centrally or can be offset to push the final position of the retractor either anterior or posterior from an initial position of tip.

In one embodiment, the handle includes a lock, such as, for example, a ratchet. In one embodiment, the ratchet includes a first tooth angled rearward, which locks the retractor blades in a closed position to avoid the retractor blades from opening prematurely. In one embodiment, the ratchet includes a plurality of teeth that are angled such that they allow for selective opening of the retractor blades while preventing the retractor blades from closing unless the ratchet is disengaged.

In one embodiment, the surgical system is employed with a method comprising the step of inserting a first dilator into an intervertebral disc space along an oblique trajectory located anterior to psoas tissue and posterior to a peritoneum and great vessels. In one embodiment, the first dilator includes a nerve integrity monitoring dilator. In one embodiment, the method includes the step of inserting an oval dilator over the first dilator with a narrow side of the oval shaped dilator positioned against the psoas muscle. In one embodiment, the method includes the step of utilizing a central cannulation disposed in the oval dilator to center retractor blades over the first dilator. In one embodiment, the method includes the step of utilizing an offset cannulation disposed in the oval dilator to position the blades posteriorly over the first dilator.

In one embodiment, the method includes the step of rotating the oval dilator from an initial position to sweep the psoas muscle laterally and loosen its attachments to the spine and displace the psoas muscle in a posterior direction. In one embodiment, the method includes the step of rotating the oval dilator back to the initial position such that a narrow side of the oval shape of the dilator is positioned against the psoas muscle. In one embodiment, the method includes the step of placing a retractor over the dilators with a handle in a practitioners right hand. This configuration places the blades without a pin hole adjacent to the psoas muscle during insertion. In one embodiment, the method includes the step of placing a retractor over the dilators with a handle in a practitioner's left hand.

In one embodiment, the method includes the step of inserting the retractor blades with its longitudinal axis in line with a longitudinal axis of a spine to facilitate placement of the retractor blades in between the psoas muscle and the peritoneum and great vessels. In one embodiment, the method includes the step of rotating the retractor 90 degrees such that the retractor blades displace and/or sweep the psoas muscle posteriorly, for example, similar to the dilator. In one embodiment, the method includes the step of positioning the retractor such that the blades are in contact with an adjacent vertebral body.

In one embodiment, the method includes the step of opening the retractor blades to remove the dilators and/or such that the retractor blades are opened wide enough to allow for plate and/or screw placement. In one embodiment, the method includes the step of pinning a superior positioned blade and/or a cephalad positioned blade to a vertebral body. In one embodiment, the method includes the step of attaching a flexible arm to the retractor to stabilize the retractor to the surgical table. In one embodiment, the method includes the step of placing a light cable with the blades and disposing the cables under a boss on a blade arm.

In one embodiment, a surgical pathway is disposed at an angle relative to a lateral axis of a patient body. In one embodiment, interbody implants and instruments are provided that facilitate positioning through the surgical pathway. In one embodiment, an interbody implant is disposed laterally in the disc space. In one embodiment, the interbody implant is positioned at an oblique angle relative to a lateral axis of the subject body. In one embodiment, the surgical pathway is oriented 0-45 degrees relative to a direct lateral axis of a subject body. In one embodiment, the surgical pathway is oriented 15-30 degrees relative to the direct lateral axis. In one embodiment, the surgical instruments are equipped with surgical navigation components, such as, for example, emitters mounted with the instruments and adjacent surgical device sensors employed with surgical navigation, microsurgical and image guided technologies that may be employed to access, view and repair spinal deterioration or damage. In one embodiment, a trial is utilized to establish a starting point for insertion of an interbody implant.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or anterolateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that al spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
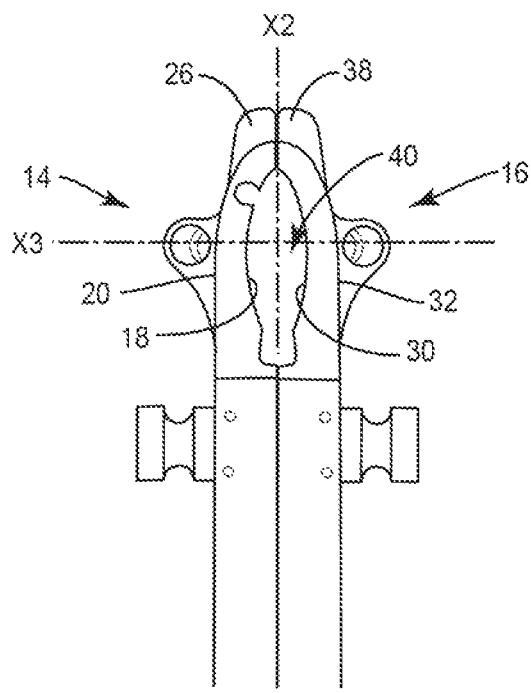
FIG. 2 is a break away, plan view of the components shown in FIG. 1.
Figure 3:
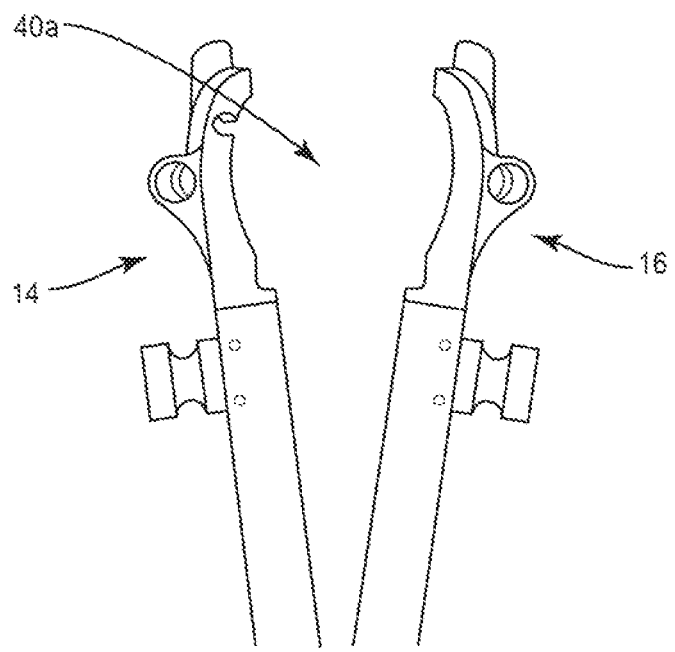
FIG. 3 is a break away, plan view of the components shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including potyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycoide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 4:
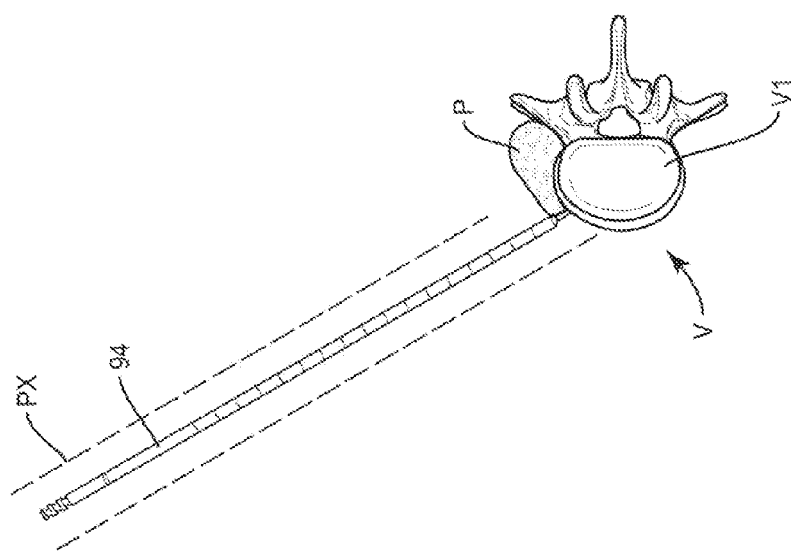
FIG. 4 is an axial view of a component of one embodiment of a system in accordance with the principles of the present disclosure disposed with vertebrae.

Spinal implant system 10 is employed, for example, with a fully open surgical procedure, a minimally invasive procedure, including percutaneous techniques, and mini-open surgical techniques to deliver and introduce instrumentation and/or an implant, such as, for example, an interbody implant, at a surgical site within a subject body of a patient, which includes, for example, a spine having vertebrae V (FIG. 4). In some embodiments, the implant can include spinal constructs, such as, for example, interbody devices, cages, bone fasteners, spinal rods, connectors and/or plates.

Figure 8:
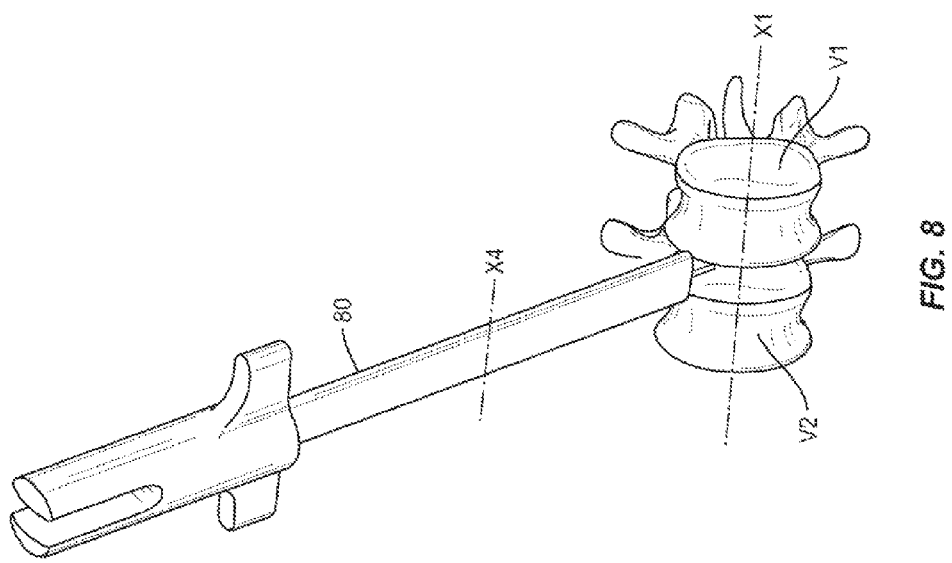
FIG. 8 is a perspective view of the components and vertebrae shown in FIG. 7.

System 10 includes a surgical instrument, such as, for example, a retractor 12 having a member, such as, for example, a blade 14. Blade 14 extends between an end 14a and an end 14b, which may comprise a blade tip. Blade 14 includes an inner surface 18 and an outer surface 20 configured for engagement with tissue, such as, for example, tissue adjacent vertebrae V. Vertebrae V defines a longitudinal axis X1 (FIG. 8).

Retractor 12 includes a member, such as, for example, a blade 16. Blade 16 extends between an end 16a and an end 16b, which may comprise a blade tip. Blade 16 includes an inner surface 30 and an outer surface 32 configured for engagement with tissue, such as, for example, tissue adjacent vertebrae V. In some embodiments, all or only a portion of blade 14 and/or blade 16 may have various cross-section configurations, such as, for example, arcuate, cylindrical, oblong, rectangular, polygonal, undulating, irregular, uniform, non-uniform, consistent, variable, and/or U-shape.

End 14b includes a tapered portion, such as, for example, a side taper 22 and surface 20 includes a projection, such as, for example, an end lip 26. End 16b includes a tapered portion, such as, for example, a side taper 34 and surface 32 includes a projection, such as, for example, an end lip 38. As such, blades 14, 16 can be inserted adjacent to psoas tissue so that tapers 22, 34 facilitate insertion with tissue and/or displace and/or bias the psoas tissue away from a surgical pathway. As blades 14, 16 are manipulated, as described herein, blades 14, 16 displace psoas tissue posteriorly relative to vertebrae V such that lips 26, 38 are disposed and/or rotated under psoas tissue and maintain the psoas tissue from sliding back under ends 14b, 16b and/or resist and prevent creeping of the psoas tissue under ends 14b, 16b. End 14b includes a concave tip surface 24 and end 16b includes a concave tip surface 36. Surfaces 24, 36 facilitate seating engagement with tissue of vertebrae V.

Blades 14, 16 are connected with a handle 50 having handles 50a, 50b, which facilitate manipulation of retractor 12 between the positions, as described herein, and relative movement of blades 14, 16 between the configurations, as described herein. Handles 50a, 50b are connected with blades 14, 16, respectively, and pivotally connected at a pivot 51 such that blade 14 can be rotated about pivot 51, in the direction shown by arrows A in FIG. 1, and blade 16 can be rotated about pivot 51, in the directions shown by arrows B.

Handle 50 includes a lock, such as, for example, a ratchet 60 configured to releasably fix handles 50a, 50b and blade 14 in a selected orientation relative to blade 16 to dispose blades in a selected configuration, as described herein. Ratchet 60 includes a rack having a locking element, such as, for example, a plurality of teeth 62 angled in a first direction and engageable with a locking pin 64 of handle 50b such that blades 14, 16 are selectively and/or incrementally adjustable to a selected configuration, as described herein.

Ratchet 60 includes a locking element, such as, for example, a tooth 66 angled in a second opposite direction to releasably fix blades 14, 16 in a closed configuration, as described herein. Tooth 66 locks blades in the closed configuration to resist and/or prevent relative movement of blades 14, 16 to an open configuration, as described herein. Teeth 62 are disposed in an angular orientation such that teeth 62 allow movement of blades 14, 16 to one or more relatively open configurations, as described herein, while resisting and/or preventing blades from relatively moving to a relatively closed configuration unless ratchet 60 is disengaged.

In one embodiment, handle 50 is disposed at an angular orientation relative to blades 14, 16. Disposal of handle 50 relative to blades 14, 16 at an angle resists and/or prevents interference with tissue during manipulation of retractor 12, such as, for example, handle 50 is configured to avoid interference with an iliac crest. In one embodiment, handle 50 is connected at an angle to force tips of blades 14, 16 to diverge and/or flare outwardly when opened such that the tips counteract tissues forces that would normally bias the retractor blades to a closed configuration. In one embodiment, handles 50a, 50b each include break away portions 52 that pivot about a pivot 54 such that portions 52 can rotate to avoid interference with tissue and/or instrumentation.

Blade 14 is movable relative to blade 16 between a closed configuration, as shown for example in FIG. 2, and an open configuration, as shown in for example, in FIG. 3, such that blades 14, 16 are spaced apart to define a surgical pathway and facilitate spacing of tissue, as described herein. In a closed configuration, blades 14, 16 are disposed in an internally rotated orientation and are movable to an open configuration such that blades 14, 16 are relatively parallel as a result of the configuration of blades 14, 16. In some embodiments, blades 14, 16 may be disposed in one or a plurality of open configurations of varying degrees of spacing of blades 14, 16, and/or configurations between open and closed configurations.

Figure 15:
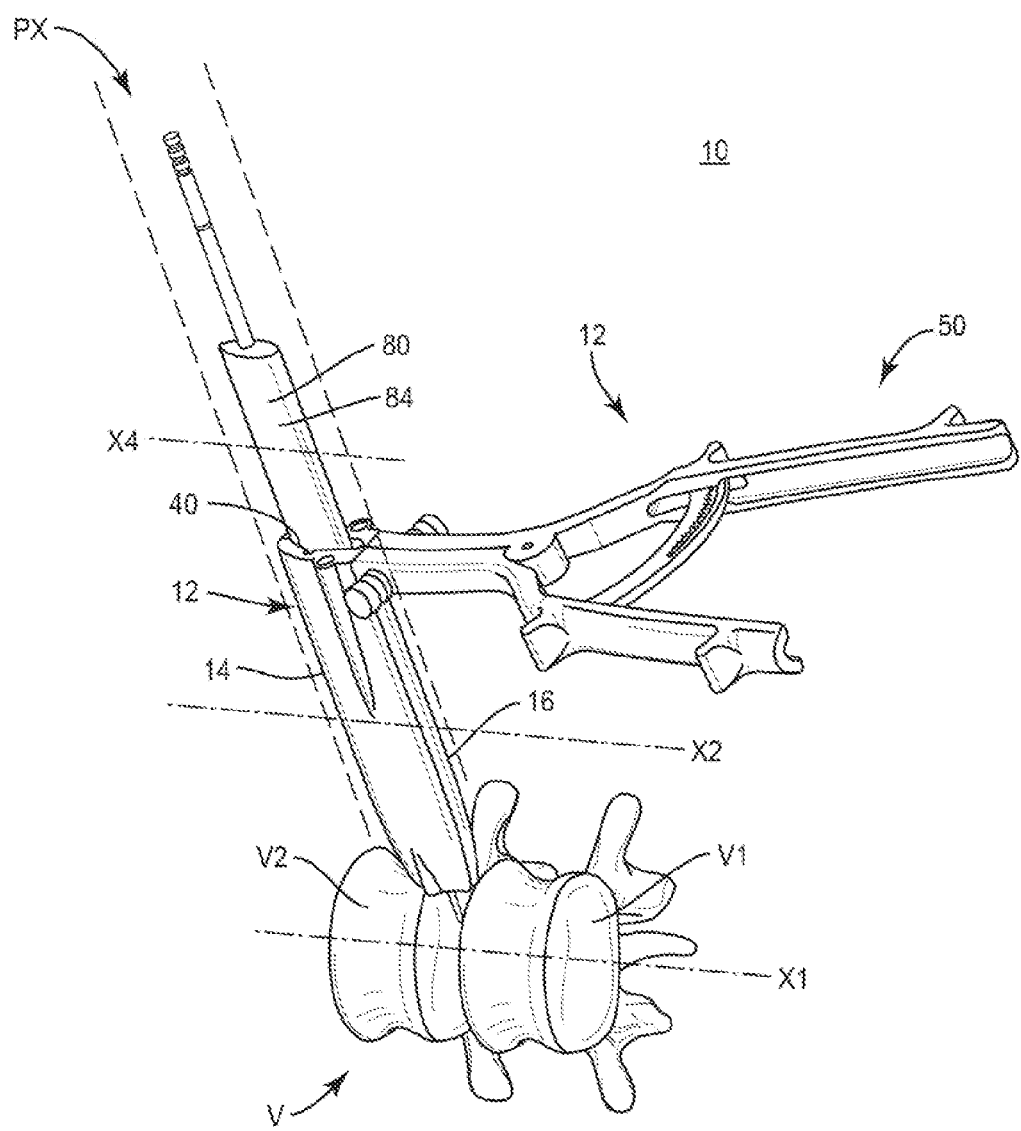
FIG. 15 is a perspective view of components of one embodiment of a system in accordance with the principles of the present disclosure disposed with vertebrae.
Figure 18:
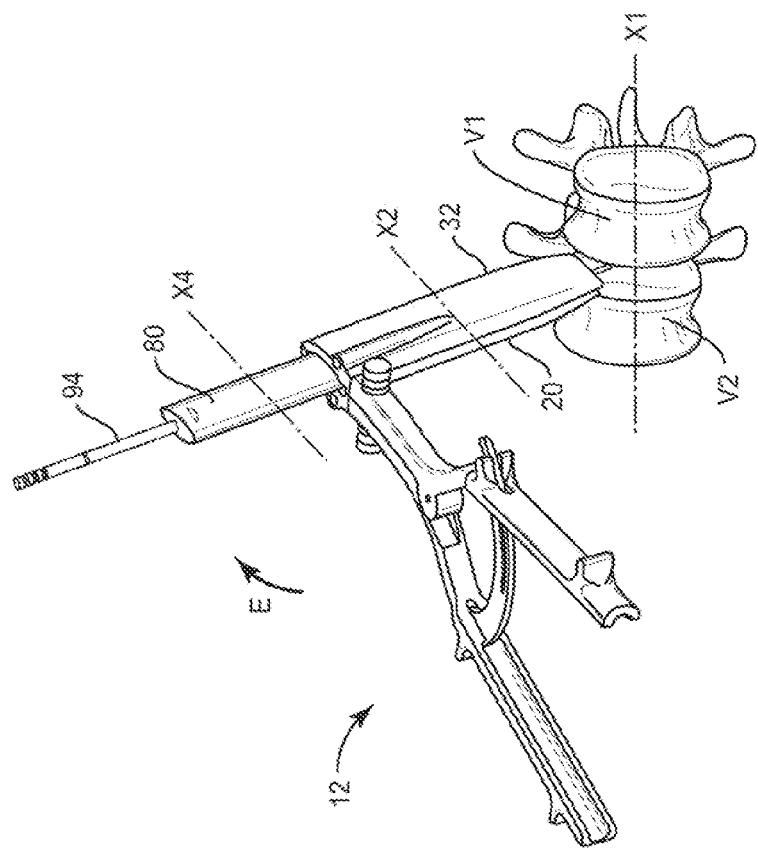
FIG. 18 is a perspective view of the components and vertebrae shown in FIG. 15.
Figure 17:
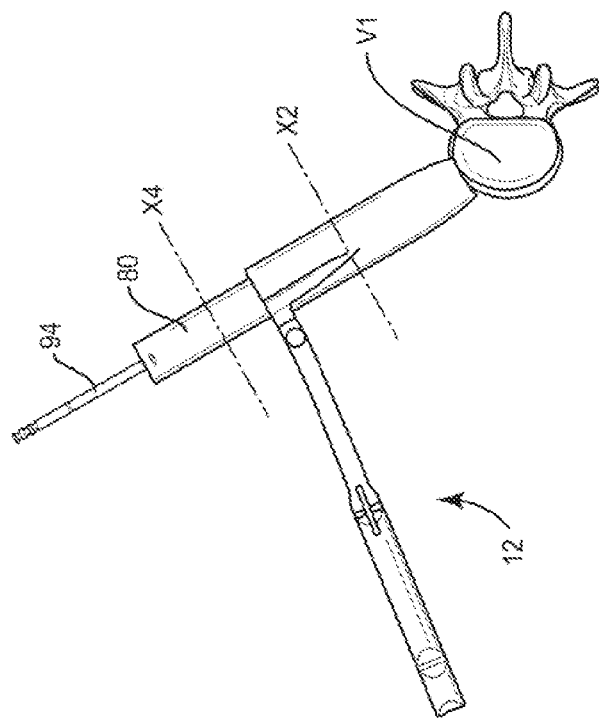
FIG. 17 is an axial view of the components and vertebrae shown in FIG. 15.
Figure 19:
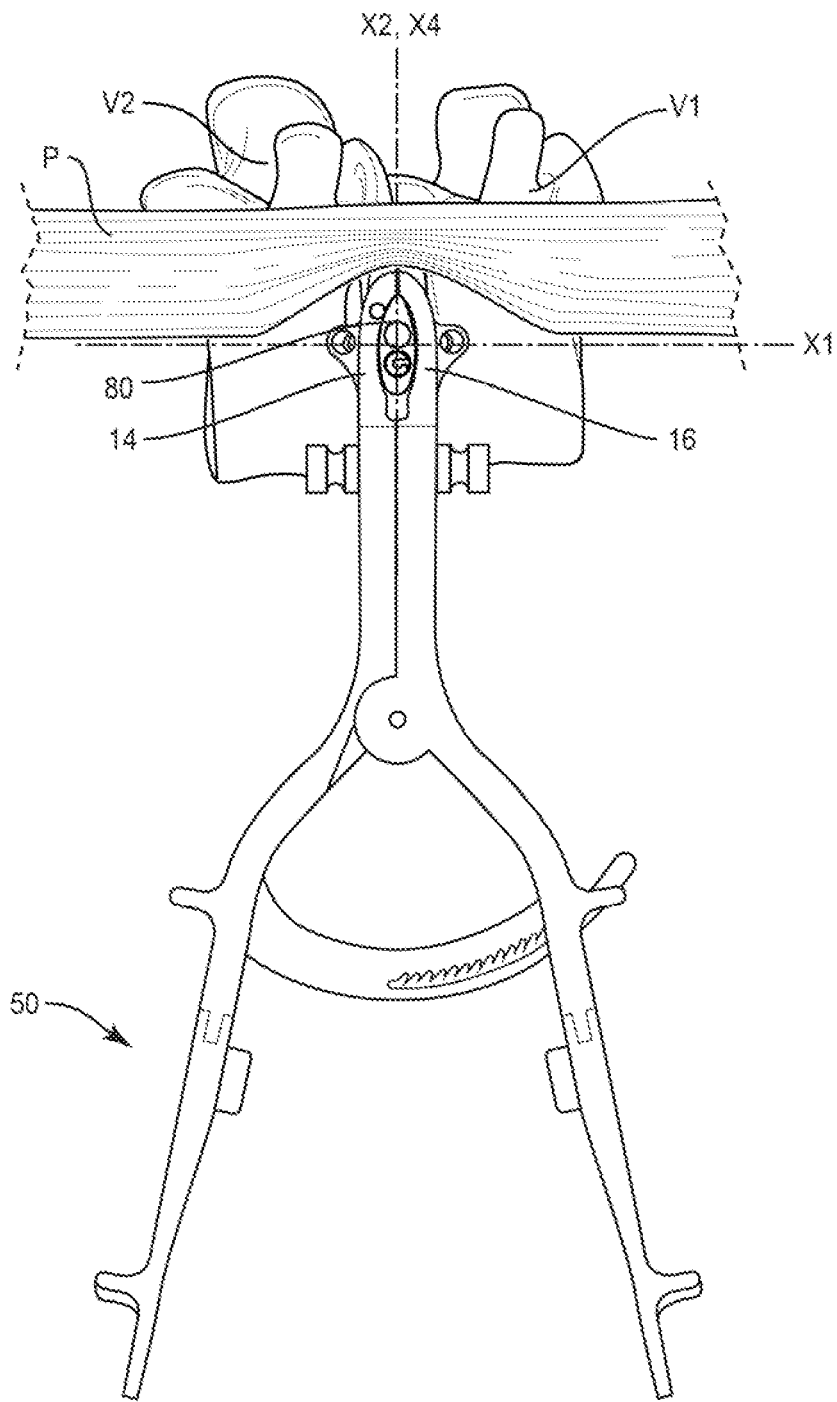
FIG. 19 is a side view of the components and vertebrae shown in FIG. 15.

In one embodiment, in the closed configuration, blades 14, 16 are disposable between a position, as shown for example in FIGS. 15 and 16, such that surfaces 18, 30 define a substantially oval cavity 40 and a position, as shown for example in FIGS. 17-19, such that blades 14, 16 are rotated to space psoas tissue, as described herein. In one embodiment, in the first position, cavity 40 comprises a substantially teardrop configuration. In some embodiments, blades 14, 16 may be rotated to one or a plurality of positions in a clockwise and/or a counter-clockwise direction to displace tissue or facilitate a surgical procedure. Cavity 40 extends along the length of blades 14, 16 and provides a pathway for surgical instruments and/or implants. Cavity 40 defines a major axis X2 and a minor axis X3.

In an initial position, as shown for example in FIGS. 15 and 16, axis X2 is disposed in substantially parallel alignment with axis X1. Blades 14, 16 are rotatable from the initial position to a position, as shown for example in FIGS. 17-19, such that axis X2 is rotated relative to axis X1 to space and/or sweep tissue, such as, for example, psoas tissue posteriorly so that blades 14, 16 can be manipulated to an open configuration to define and create a working channel 40a for a surgical pathway. Rotation of blades 14, 16 causes surfaces 20, 32 to apply pressure against psoas tissue to displace psoas muscle, vertebral tissue and/or adjacent tissue posteriorly relative to the spine. In some embodiments, retractor 12 may displace tissue in alternate directions, such as, for example, anteriorly, laterally, caudal and/or cephalad.

System 10 includes a surgical instrument, such as, for example, a dilator 94 and a surgical instrument, such as, for example, a dilator 80, as shown in FIG. 1. Dilator 80 has an outer surface 84 and includes an oval cross-section configuration. Dilator 80 extends between an end 86 and an end 88. Dilator 80 defines a major axis X4 and a minor axis X5. Dilator 80 is disposable between an initial position, as shown for example in FIGS. 15 and 16, and a position, as shown for example in FIGS. 17-19, such that surface 84 is rotated to space psoas tissue, as described herein. In one embodiment, in the first position, the cross-section of dilator 80 comprises a substantially teardrop configuration. In some embodiments, dilator 80 may be rotated to one or a plurality of positions in a clockwise and/or a counter-clockwise direction to displace tissue or facilitate a surgical procedure.

Figure 9:
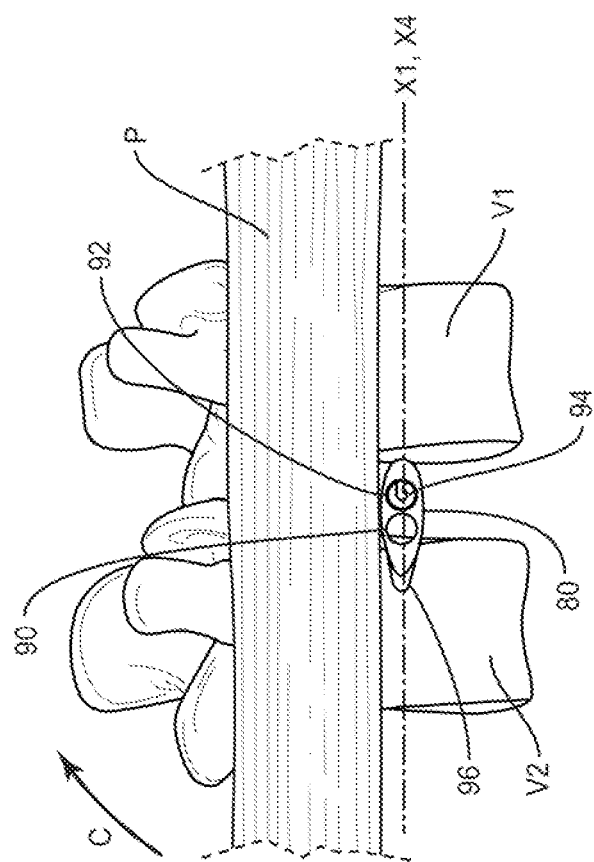
FIG. 9 is a side view of the components and vertebrae shown in FIG. 7.

In the initial position, as shown for example in FIGS. 15 and 16, axis X4 is disposed in substantially parallel alignment with axis X1. Dilator 80 is rotatable from the initial position to a position, as shown for example in FIGS. 17-19, such that axis X4 is rotated relative to axis X1 to space and/or sweep tissue, such as, for example, psoas tissue posteriorly. Rotation of dilator 80 causes surface 84 to apply pressure against psoas tissue to displace psoas muscle, vertebral tissue and/or adjacent tissue posteriorly relative to the spine. In some embodiments, dilator 80 may displace tissue in alternate directions, such as, for example, anteriorly, laterally, caudal and/or cephalad. In one embodiment, surface 84 includes a projection, such as, for example, an end lip 98 (FIG. 9). As dilator 80 and/or blades 14, 16 are manipulated, as described herein, dilator 80 and/or blades 14, 16 displace psoas tissue posteriorly relative to vertebrae V such that lip 98 is disposed and/or rotated under psoas tissue and maintains the psoas tissue from sliding back under end 88 and/or resists and prevents creeping of the psoas tissue under end 88. End 88 includes a concave tip surface 96 that facilitates seating engagement with tissue of vertebrae V.

Dilator 80 defines a central cannulation 90 configured for disposal of dilator 94. In some embodiments, dilator 80 can include an offset cannulation that communicates with cannulation 90 and facilitates offset translation of retractor 12 anteriorly to a final position from an initial position of dilator 94. In one embodiment, dilator 80 can include an offset cannulation that is spaced from cannulation 90 and facilitates offset translation of retractor 12 posteriorly to a final position from an initial position of dilator 94.

In some embodiments, spinal implant system 10 may comprise various surgical instruments, such as, for example, drivers, extenders, reducers, spreaders, distractors, clamps, forceps, elevators and drills, which may be alternately sized and dimensioned, and arranged as a kit. In some embodiments, spinal implant system 10 may comprise the use of microsurgical and image guided technologies, such as, for example, surgical navigation components employing emitters and sensors, which may be employed to track introduction and/or delivery of the components of spinal implant system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

In one embodiment, in assembly, operation and use, as shown in FIGS. 4-22, spinal implant system 10, similar to the systems described herein, is employed with a surgical procedure for treatment of a spinal disorder, such as those described herein, affecting a section of a spine of a patient. Spinal implant system 10 may also be employed with other surgical procedures. To treat the affected section of vertebrae V of a subject body, the subject body is disposed in a side orientation relative to a surgical fixed surface, such as, for example, a surgical table configured for supporting the subject body. The subject body is placed on a side, left side up such that the vena cava, being oriented to the right of a centerline of the subject body, is positioned further away from a surgical pathway PX, as shown in FIG. 4 and described herein.

The subject body is oriented such that an OLIF procedure can be performed obliquely in front of a psoas muscle P to provide direct access to one or more intervertebral spaces of L2-L5 vertebral levels of vertebrae V while avoiding selected muscular and abdominal anatomical structures, such as, for example anterior vasculature. In some embodiments, placement of the subject body on its side facilitates access to surgical pathway PX that is disposed at an oblique angle. In some embodiments, placement of the subject body on its side facilitates natural movement of the abdominal contents away from surgical pathway PX via the effect of gravity.

In some embodiments, electrodes, such as, for example, electrodes used with neural integrity monitoring systems, may not be necessary as the pathway PX may avoid nerve roots as well as the neural structures in psoas muscle P that are encountered along a lateral approach. In some embodiments, psoas muscle P is completely paralyzed during the surgical procedure as there is no need to monitor or locate nerves present in psoas muscle P as psoas muscle P is avoided along the oblique surgical pathway PX. Paralyzing psoas muscle P facilitates manipulation and/or retraction of psoas muscle P during the surgical procedure.

The L2 and L5 disc spaces, lower ribs and iliac crest can be marked on the skin as landmarks. In some embodiments, for example, a single vertebral level procedure, the subject body is marked 4-10 centimeters (cm) anterior to the midsection of the target disc (or approximately one third of the distance from the top of the iliac crest to the umbilicus). A 3 cm to 6 cm vertical, horizontal or oblique incision is made in tissue of the subject body. In some embodiments, for example, a two vertebral level procedure, the subject body is marked 4-10 cm anterior to the midsection of the intervening vertebral body and an incision is made in tissue of the subject body. In one embodiment, the lumbar lordosis of the operative levels can be marked on the skin to determine the angle in line with the disc space.

In some embodiments, the subcutaneous fat layers are dissected until the abdominal musculature is reached. In some embodiments, a mono-polar cautery can be utilized for hemostasis, and a small self-retaining retractor can be used for initial dissection of the skin and subcutaneous layer. In some embodiments, the external oblique fascia is the first plane encountered and is the only layer that will need to be sharply incised. In some embodiments, a clamp is used to bluntly spread through the fibers of the external oblique, internal oblique, and transversalis muscles. In some embodiments, dissection is performed in line with the muscle fibers as these muscle layers extend in opposite directions.

In some embodiments, an index finger is utilized to follow the internal abdominal wall posteriorly down to psoas muscle P. In some embodiments, a finger or a blunt instrument is used to sweep the peritoneal contents, including the ureter, which reflects with the peritoneum, and the retroperitoneal fat anteriorly past the anterior portion of psoas muscle P clearing to the anterior vertebral body.

Figure 5:
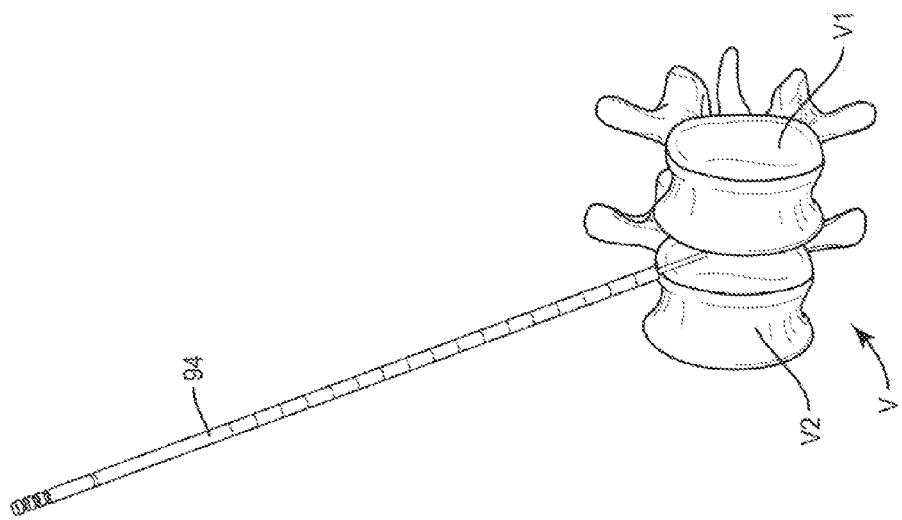
FIG. 5 is a perspective view of the component and vertebrae shown in FIG. 4.
Figure 7:
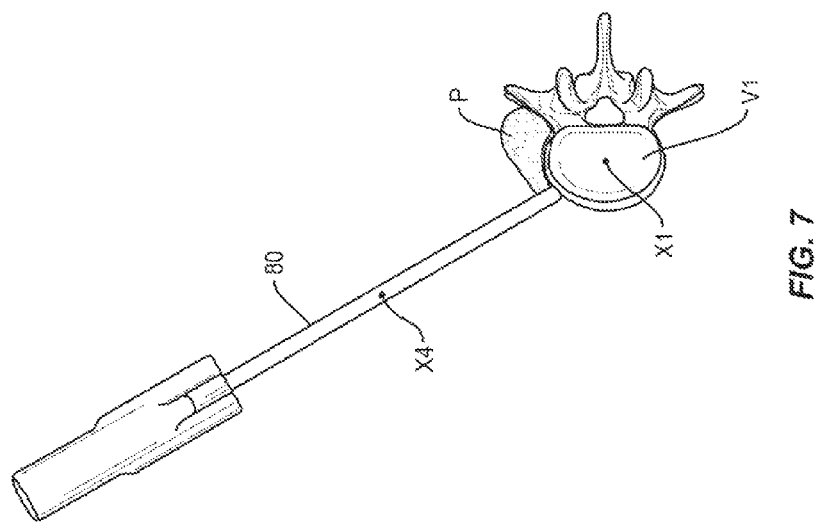
FIG. 7 is an axial view of components of one embodiment of a system in accordance with the principles of the present disclosure disposed with vertebrae.

Dilator 94 is initially inserted into the disc space between vertebra V1 and vertebra V2 along an oblique trajectory along surgical pathway PX, as shown in FIGS. 4-6, anterior relative to psoas muscle P and posterior to a peritoneum (not shown). Dilator 80 is inserted over dilator 94 such that axis X4 of dilator 80 is aligned with axis X1, as shown in FIGS. 7-9. In some embodiments, as shown in FIG. 9, dilator 94 is disposed with offset cannulation 92 for translation, as described herein. In some embodiments, dilator 94 is disposed with center cannulation 90 for a centered alignment over dilator 94.

Figure 11:
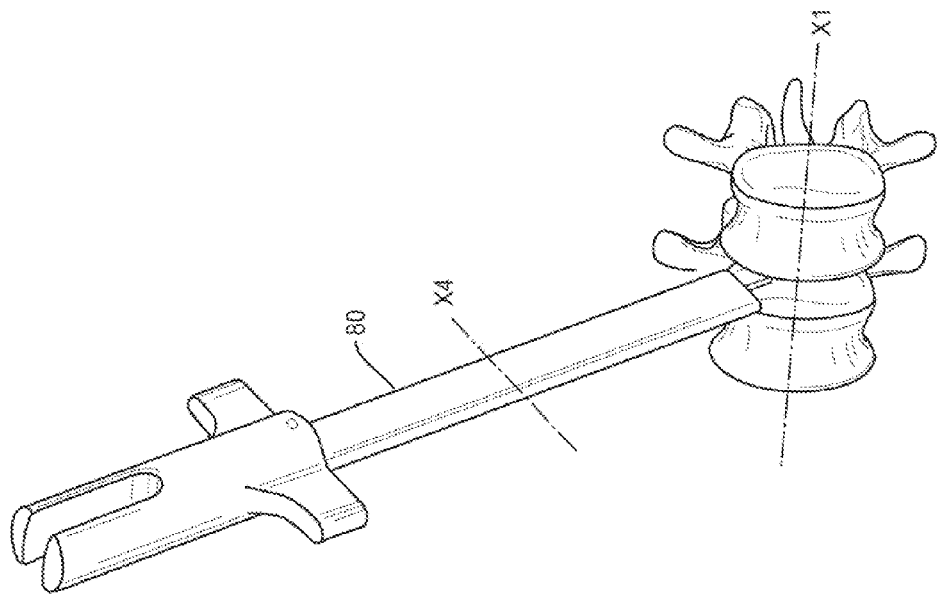
FIG. 11 is a perspective view of the components and vertebrae shown in FIG. 7.
Figure 10:
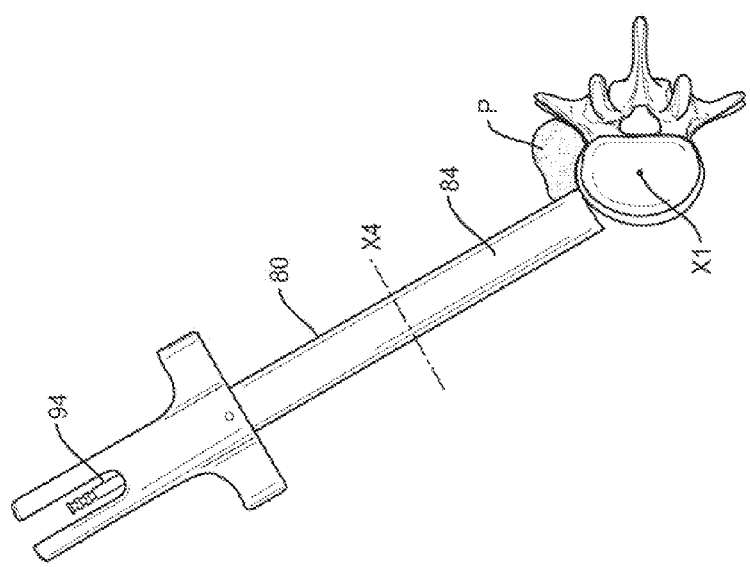
FIG. 10 is an axial view of the components and vertebrae shown in FIG. 7.
Figure 12:
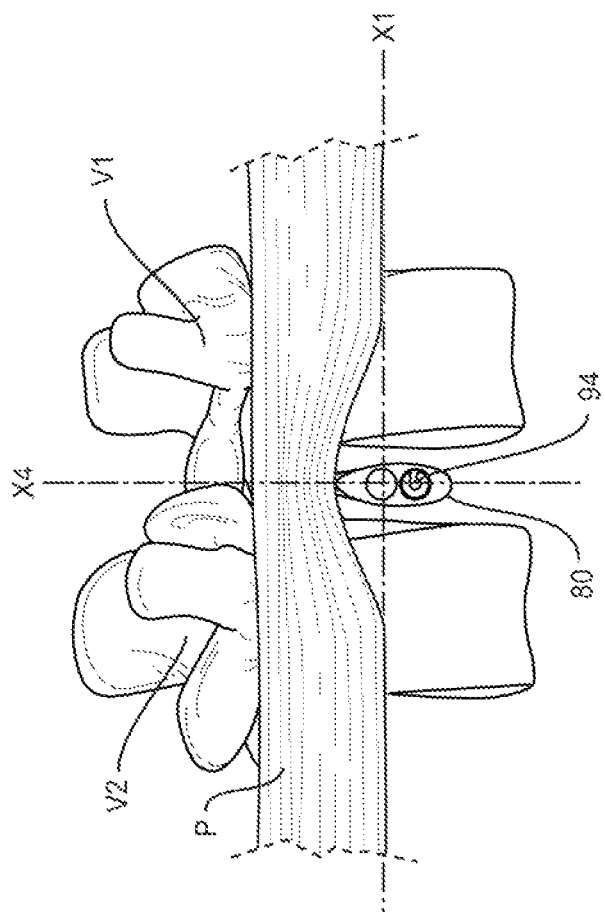
FIG. 12 is a side view of the components and vertebrae shown in FIG. 7.
Figure 13:
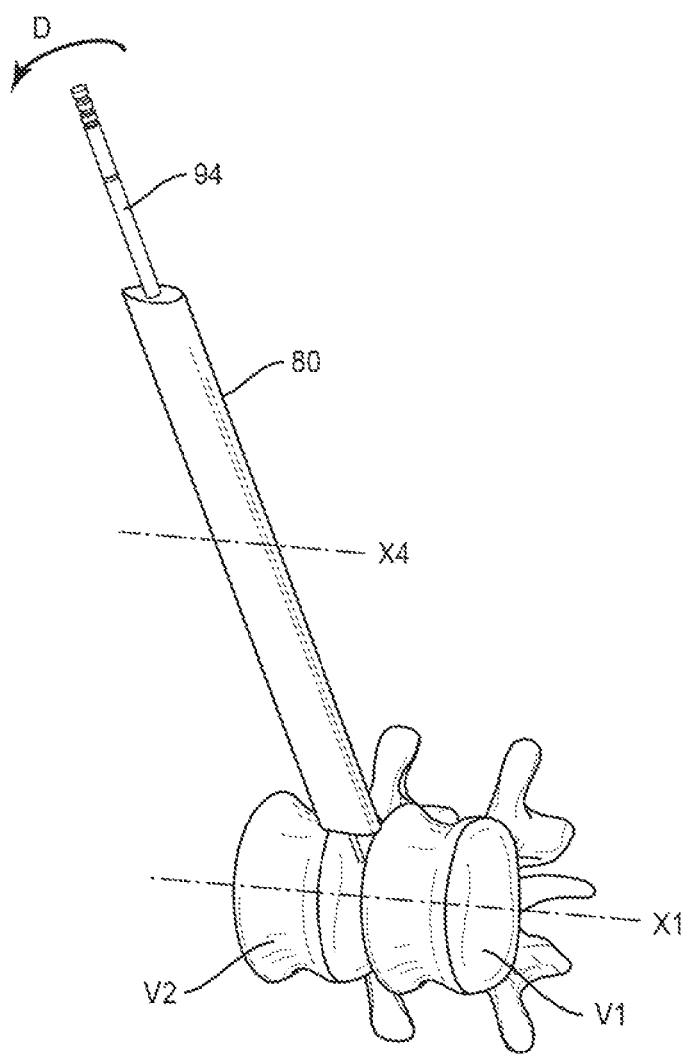
FIG. 13 is a perspective view of components and the vertebrae shown in FIG. 7.
Figure 14:
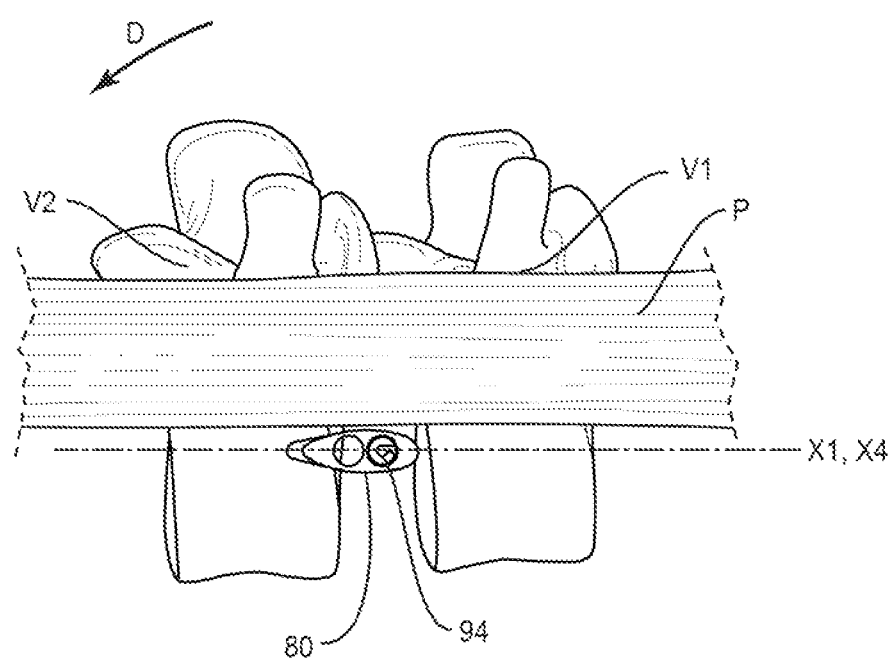
FIG. 14 is a side view of the components and vertebrae shown in FIG. 13.

Dilator 80 is rotated, in the direction shown by arrow C in FIG. 9, such that axis X4 is rotated relative to axis X1. Dilator 80 is rotated substantially 90 degrees, as shown in FIGS. 10-12, such that axis X4 is substantially perpendicular to axis X1 to displace and space psoas muscle P and/or tissue posteriorly relative to vertebrae V and loosen its attachments to vertebrae V. Rotation of dilator 80 causes surface 84 to apply pressure against psoas muscle P to sweep psoas muscle P posteriorly relative to the spine. Dilator 80 is rotated 90 degrees, in the direction shown by arrow D in FIGS. 13 and 14, such that dilator 80 returns to the initial position and axes X1, X4 are aligned.

Retractor 12 is disposed in a closed configuration in a position, as shown in FIGS. 15 and 16, such that blades 14, 16 form cavity 40 and are introduced along an oblique trajectory along surgical pathway PX. In one embodiment, retractor 12 is manipulated such that dilator 80 is disposed with cavity 40 by a practitioner holding handle 50 with a right hand. Retractor 12 is inserted over dilators 80, 94 and positioned adjacent vertebrae V1, V2 such that axes X1, X2 are disposed in alignment. In some embodiments, retractor 12 can be locked in a closed configuration with ratchet 60, as described herein.

Retractor 12 is rotated, in the direction shown by arrow E in FIG. 18, approximately 90 degrees into a position, as shown in FIGS. 17-19, such that blades 14, 16 displace and space psoas muscle P and/or tissue posteriorly relative to vertebrae V and loosen its attachments to vertebrae V. Blades 14, 16 are rotated substantially 90 degrees and such rotation causes axes X2, X4 to rotate relative to axis X1. Rotation of blades 14, 16 causes surfaces 20, 32 to apply pressure against psoas muscle P to sweep psoas muscle posteriorly relative to the spine.

Figure 20:
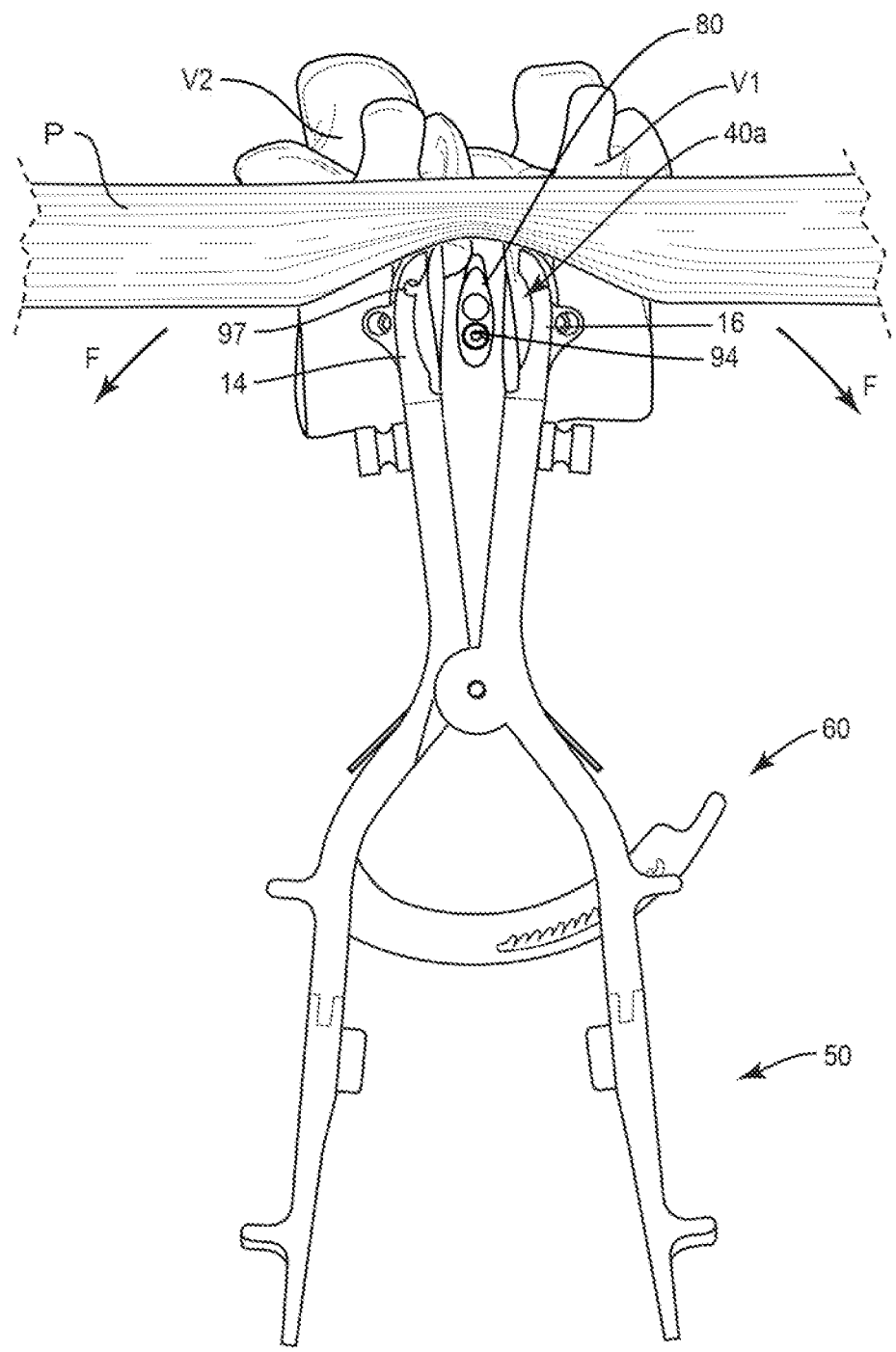
FIG. 20 is a side view of the components and vertebrae shown in FIG. 15.
Figure 21:
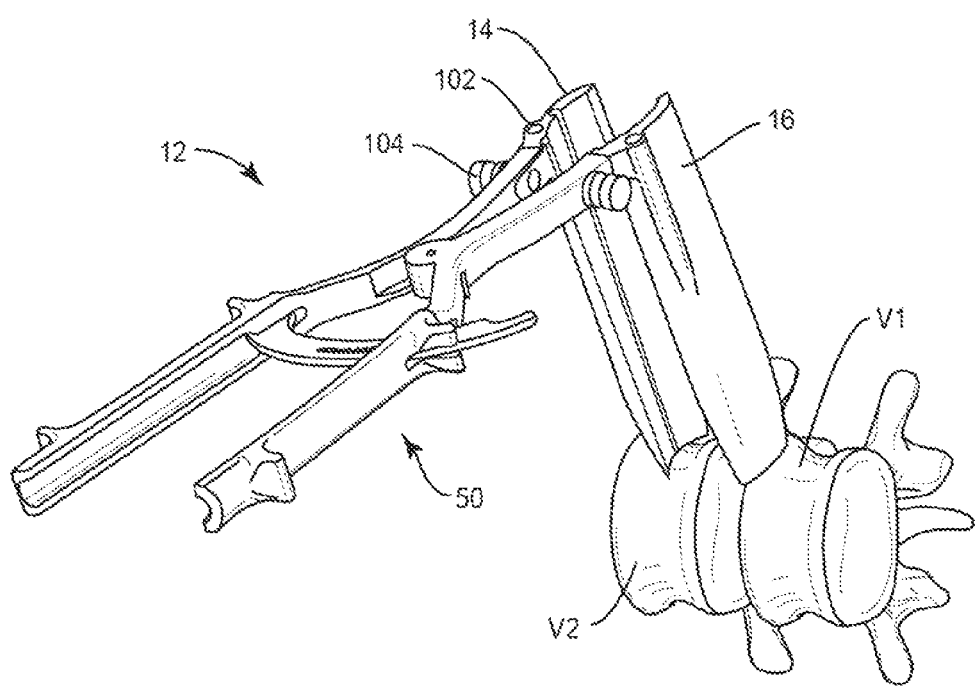
FIG. 21 is a perspective view of components and vertebrae shown in FIG. 15.
Figure 22:
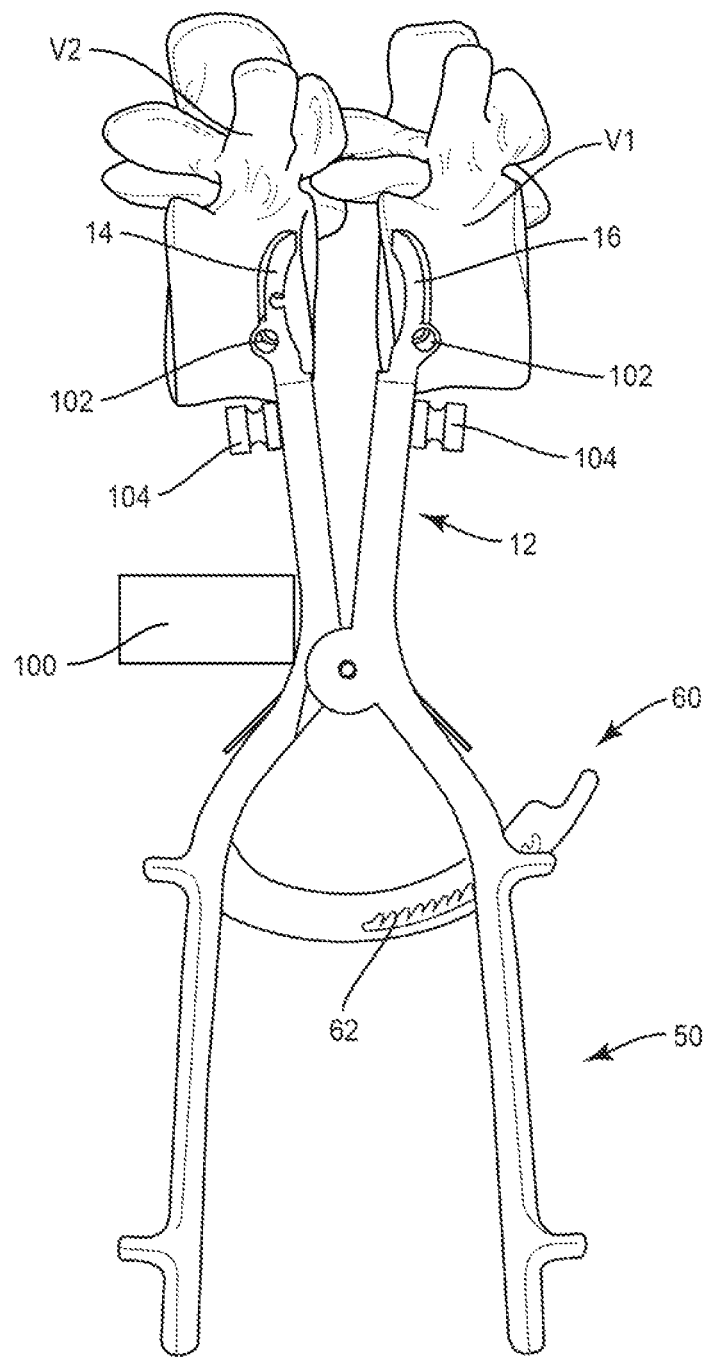
FIG. 22 is a side view of one embodiment of the components and vertebrae shown in FIG. 15.

Retractor 12 is manipulated, which may include releasing ratchet 60 from a locked orientation, from the closed configuration such that blades 14, 16 are rotated, in the direction shown by arrows F in FIG. 20, to dispose retractor 12 in an open configuration, as shown in FIGS. 20-22. Dilators 80, 94 are removed. In some embodiments, blade 14 is a cephalad blade and pinned to vertebra V2 via a pin hole 97 to stabilize retractor 12 with vertebrae V. Blades 14, 16 are spaced to define a working channel 40a aligned with surgical pathway PX to facilitate introduction of implants, constructs and/or surgical instrumentation, as described herein, along an oblique trajectory along surgical pathway PX.

In one embodiment, a flex arm 100 is connected with handle 50 to stabilize retractor 12 by connecting retractor 12 to a surgical table, as shown in FIG. 22. In some embodiments, OLIF light cables (not shown) are disposed with blades 14, 16, via openings 102 and the cables are routed around bosses 104.

In some embodiments, a discectomy is performed via surgical pathway PX with channel 40a of retractor 12. In some embodiments, instruments, such as, for example, a Cobb, mallet, shaver, serrated curettes, rasp, a ring curette, a uterine curette and/or combo tools are utilized to perform a discectomy of the disc space. In some embodiments, the instruments enter the subject body obliquely through retractor 12 and can be turned orthogonally to allow the surgeon to work orthogonally across the disc space. The disc space is distracted until adequate disc space height is obtained.

In some embodiments, an anterior longitudinal ligament (ALL) release procedure can be performed using an OLIF approach post-discectomy. For example, loosening the ALL can be performed by placing holes or partial cuts in the ALL such that the OLIF surgical pathway is immediately closer to the ALL.

In some embodiments, trial implants (not shown) are delivered along surgical pathway PX and channel 40a of retractor 12. The trial implants are used to distract one or more intervertebral spaces of the L2-L5 vertebral levels and apply appropriate tension in the intervertebral space allowing for indirect decompression. In one embodiment, a direct decompression of the disc space is performed by removing a portion of a herniated disc. In some embodiments, one or a plurality of interbody implants can be introduced and delivered along surgical pathway PX and channel 40a for implantation with one or more intervertebral spaces of the L2-L5 vertebral levels.

In some embodiments, pilot holes or the like are made in vertebrae V1, V2 adjacent its intervertebral space, via surgical pathway PX and channel 40a for receiving bone fasteners and/or attaching spinal constructs, which may include rods and plates. An inserter is attached with the implants and/or spinal constructs for delivery along surgical pathway PX and channel 40a adjacent to a surgical site for implantation adjacent one or more vertebra and/or intervertebral spaces of the L2-L5 vertebral levels.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of spinal implant system 10. In some embodiments, spinal implant system 10 may include implants and/or spinal constructs, which may include one or a plurality of plates, rods, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft allograft, xenograft, autograft, bone paste, bone chips, Skelite®, and/or BMP to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration. In such embodiments, titanium coatings may be applied via a variety of methods, including but not limited to plasma spray coating and/or mechanical attachment of titanium plates to form a PEEK/Titanium implant.

In one embodiment, as shown in FIGS. 23-27, spinal implant system 10, similar to the systems and methods described herein, comprises retractor 12 described herein, having blades 214, 216 similar to blades 14, 16 described herein. Blade 214 extends between an end 214a and an end 214b. Blade 214 includes an inner surface 218 and an outer surface 220 configured for engagement with tissue, similar to that discussed with regard to the embodiments described herein. Surface 218 defines a mating element, such as, for example, a longitudinal groove 240 extending between ends 214a, 214b. Groove 240 comprises a uniformly configured channel disposed in substantially co-axial or parallel alignment with a longitudinal axis of blade 214. In some embodiments, groove 240 may extend along all or only a portion of surface 218. In some embodiments, groove 240 may extend in alternate orientations relative to a longitudinal axis of blade 214, such as, for example, transverse, angular, offset and/or staggered. Blade 214 includes pin hole 297, similar to pin hole 97 described herein. In some embodiments, pin hole 297 is disposed with a superior blade and adjacent an edge surface of the blade.

Blade 216 extends between an end 216a and an end 216b. Blade 216 includes an inner surface 230 and an outer surface 232 configured for engagement with tissue, similar to that discussed with regard to the embodiments described herein. Surface 230 defines a mating element, such as, for example, a longitudinal groove 242 extending between ends 216a, 216b. Groove 242 comprises a uniformly configured channel disposed in substantially co-axial or parallel alignment with a longitudinal axis of blade 216. In some embodiments, groove 242 may extend along all or only a portion of surface 230. In some embodiments, groove 242 may extend in alternate orientations relative to a longitudinal axis of blade 216, such as, for example, transverse, angular, offset and/or staggered.

Figure 23:
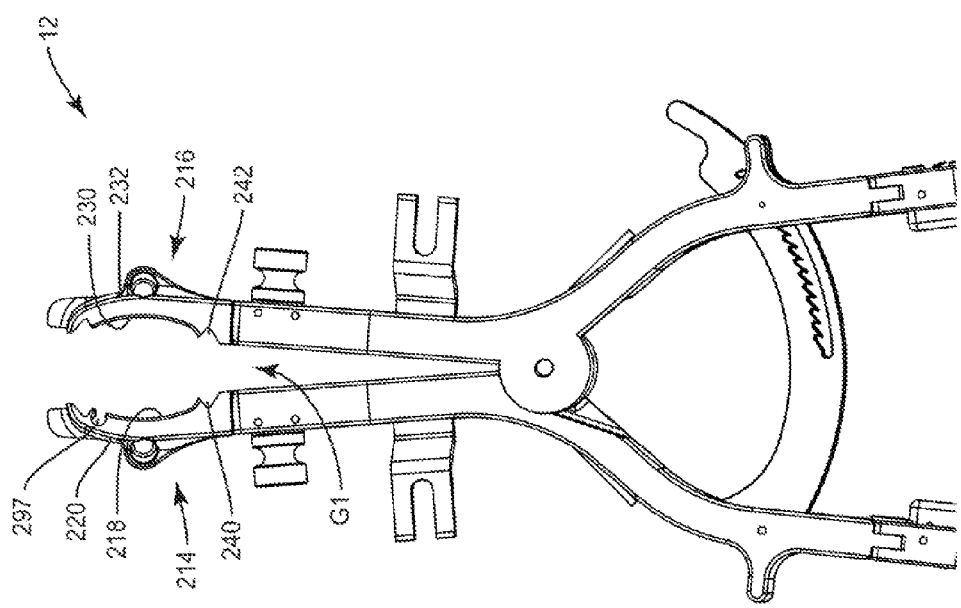
FIG. 23 is a break away plan view of components of one embodiment of a system in accordance with the principles of the present disclosure.

Grooves 240, 242 are configured to receive a member, such as, for example, a blade 302, which is an independent component of system 10 and separately attachable with retractor 12 in an interlocking configuration. In one embodiment, blade 302 is interlocked with blades 214, 216 in a dovetail connection. In some embodiments, in an open configuration of blades 214, 216, similar to and as described herein with regard to blades 14, 16, groove 240 is spaced from groove 242, as shown in FIG. 23.

Figure 24:
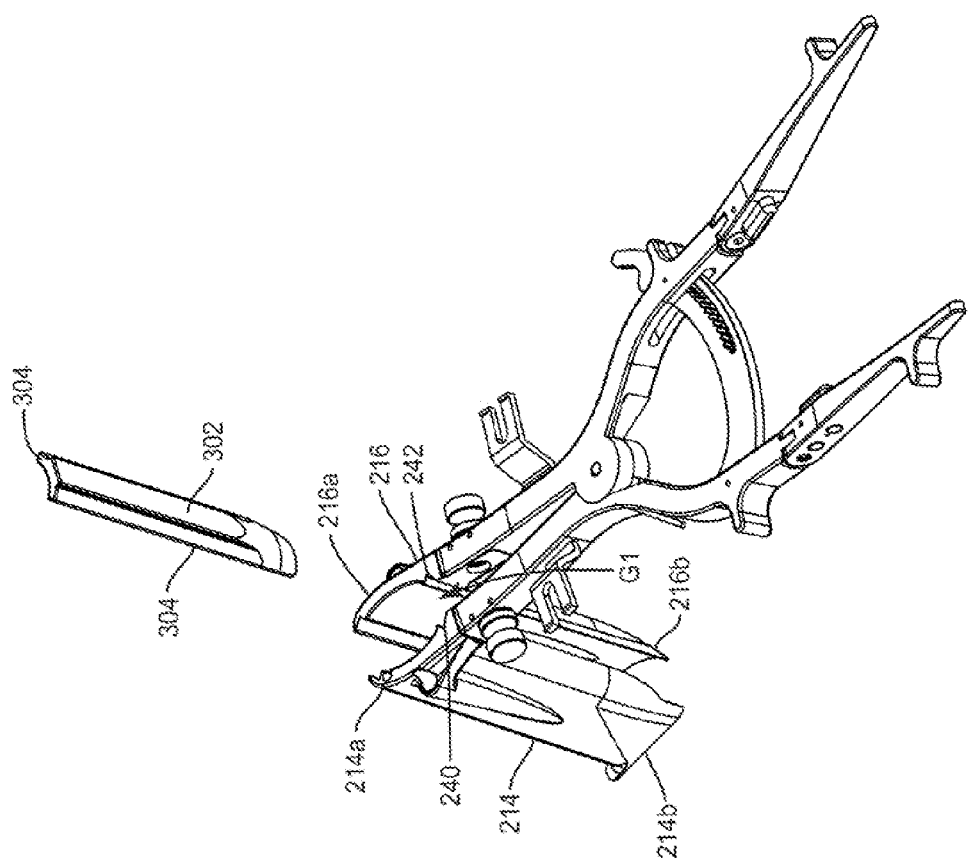
FIG. 24 is a perspective view of components of the system shown in FIG. 23.
Figure 25:
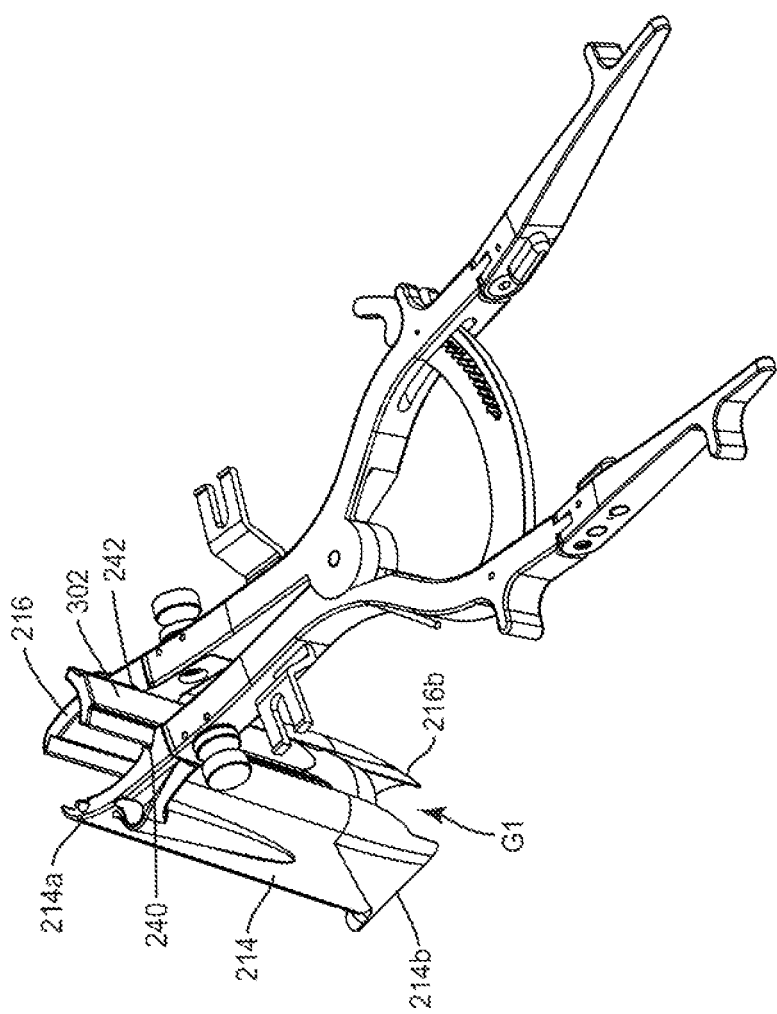
FIG. 25 is a perspective view of components of the system shown in FIG. 23.

Blade 302 is oriented for alignment with blades 214, 216 and grooves 240, 242, as shown in FIG. 24. Mating elements, such as, for example, flanges 304, disposed on sides of blade 302, are oriented for alignment with grooves 240, 242. Flanges 304 are manipulated for slidable engagement with surfaces 218, 230 such that blade 302 axially translates relative to blades 214, 216 for assembly with retractor 12, as shown in FIG. 25.

Figure 26:
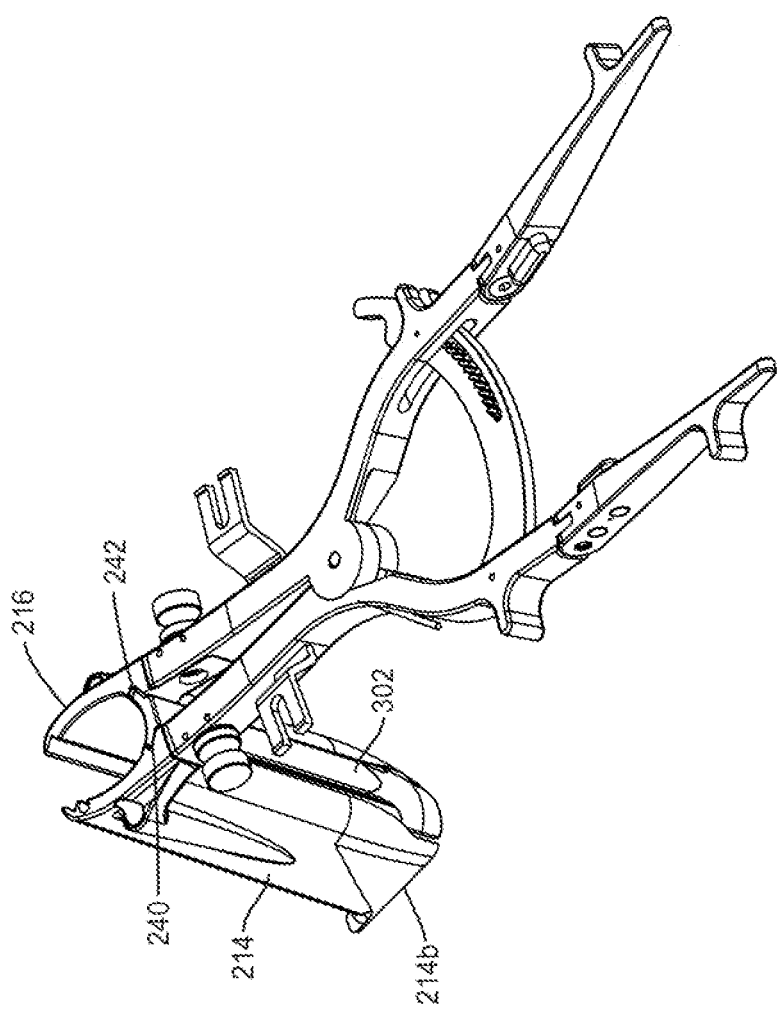
FIG. 26 is a perspective view of components of the system shown in FIG. 23.
Figure 27:
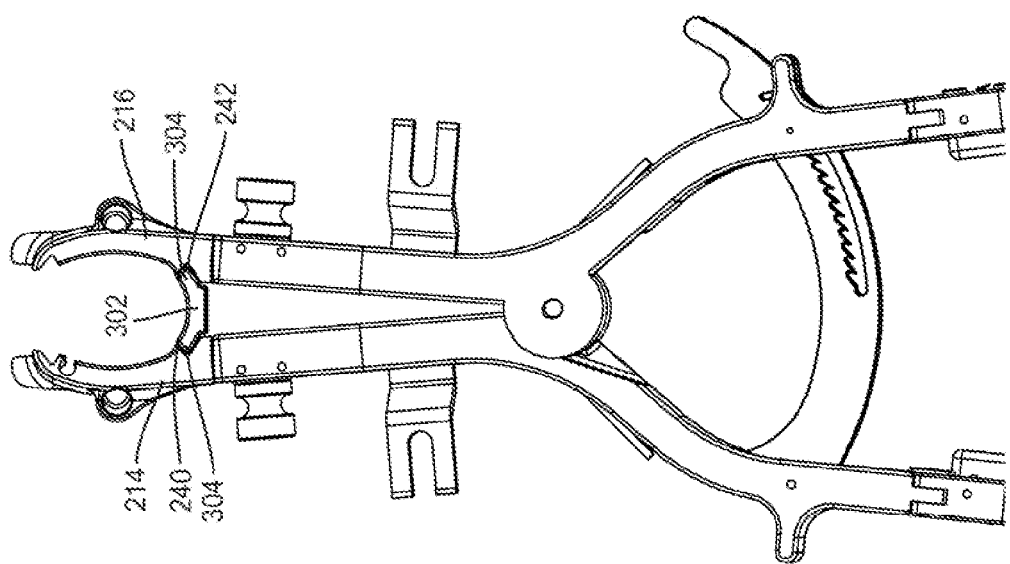
FIG. 27 is a break away plan view of components of the system shown in FIG. 23.

Blade 302 is selectively translated relative to blades 214, 216 and in an interlocking configuration with grooves 240, 242 to partially close and/or fully close a gap G1 of blades 214, 216. In some embodiments, blade 302 is adjustable to partially close gap G1, as shown in FIG. 25. In some embodiments, blade 302 is disposed in alignment with the ends of blades 214, 216 to fully close gap G1, as shown in FIG. 26. In some embodiments, disposal of blade 302 with blades 214, 216 partially encloses a surgical pathway, as described for example, in connection with use of retractor 12 herein. In some embodiments, blade 302 may be disposed with blades 214, 216, as described herein, in various surgical approaches to the spine, including anterior, posterior, posterior mid-line, direct lateral, postero-lateral, and/or antero-lateral approaches, and in other body regions, to partially close or fully close gap G1 and/or partially enclose a surgical pathway.

In some embodiments, grooves 240, 242 are disposed adjacent to an anterior portion of blades 214, 216 relative to an orientation of retractor 12 with a surgical site and/or vertebrae, see, for example, that shown with regard to FIGS. 20 and 21. This configuration orients blade 302 with blades 214, 216 to close an anterior gap and/opening, such as, for example, gap G1 between blades 214, 216. In some embodiments, groove 240 and/or groove 242 may be variously disposed with blades 214, 216. In some embodiments, blade 302 may be variously configured and dimensioned to accommodate variously configured and dimensioned retractor gaps and/or openings.

In one embodiment, as shown in FIGS. 28-31, retractor 12 includes blades 214, 216, described with regard to FIGS. 23-27, having blade 302 disposed with grooves 240, 242 and a blade 502. Surface 218 includes groove 240, described herein, and defines a mating element, such as, for example, a longitudinal groove 440 spaced from groove 240 and extending between ends 214a, 214b. Groove 440 comprises a uniformly configured channel disposed in substantially co-axial or parallel alignment with a longitudinal axis of blade 214. In some embodiments, groove 440 may extend along all or only a portion of surface 218. In some embodiments, groove 440 may extend in alternate orientations relative to a longitudinal axis of blade 214, such as, for example, transverse, angular, offset and/or staggered.

Surface 230 includes groove 242, described herein, and defines a mating element, such as, for example, a longitudinal groove 442 spaced from groove 242 and extending between ends 216*a*, 216*b*. Groove 442 comprises a uniformly configured channel disposed in substantially co-axial or parallel alignment with a longitudinal axis of blade 216. In some embodiments, groove 442 may extend along all or only a portion of surface 230. In some embodiments, groove 442 may extend in alternate orientations relative to a longitudinal axis of blade 216, such as, for example, transverse, angular, offset and/or staggered.

Grooves 440, 442 are configured to receive a member, such as, for example, blade 502, which is an independent component of system 10 and separately attachable with retractor 12 in an interlocking configuration. In one embodiment, blade 502 is interlocked with blades 214, 216 in a dovetail connection. In some embodiments, in an open configuration of blades 214, 216, similar to and as described herein with regard to blades 14, 16, groove 440 is spaced from groove 442, as shown in FIG. 28.

Figure 28:
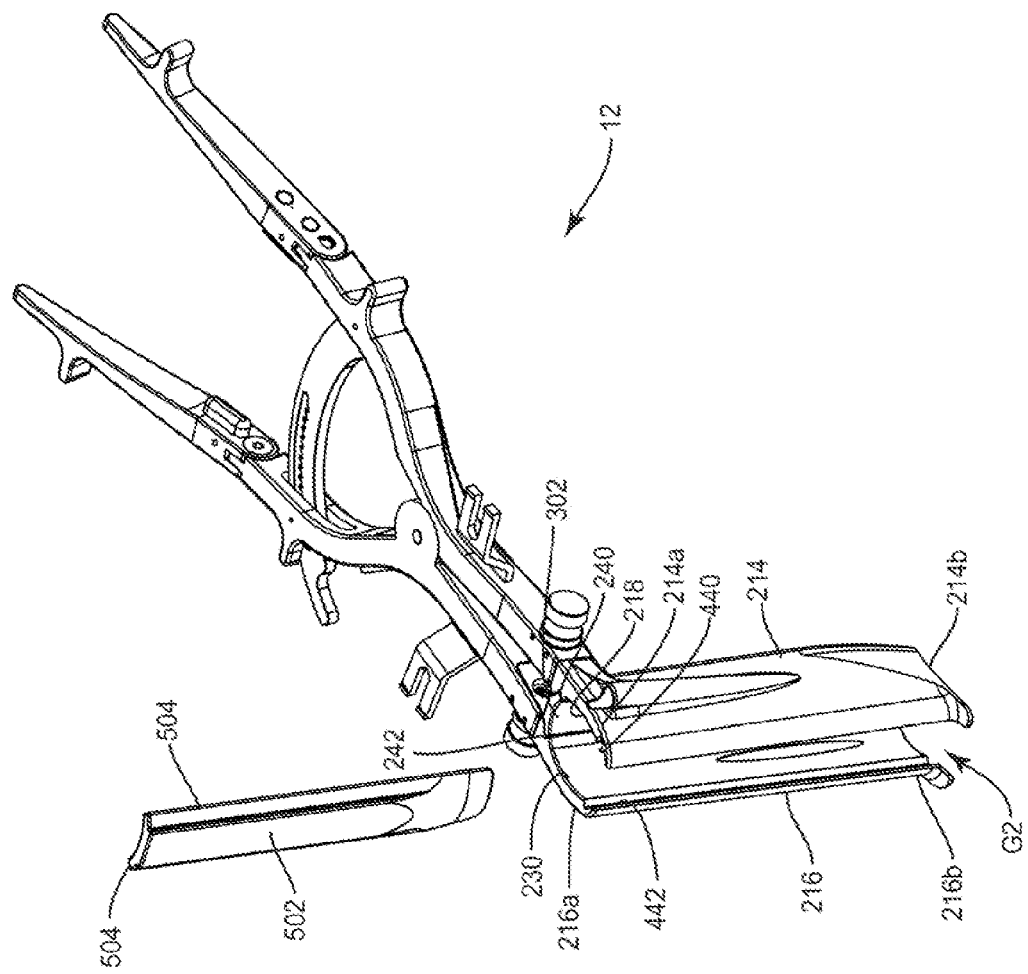
FIG. 28 is a perspective view of components of one embodiment of a system in accordance with the principles of the present disclosure.
Figure 29:
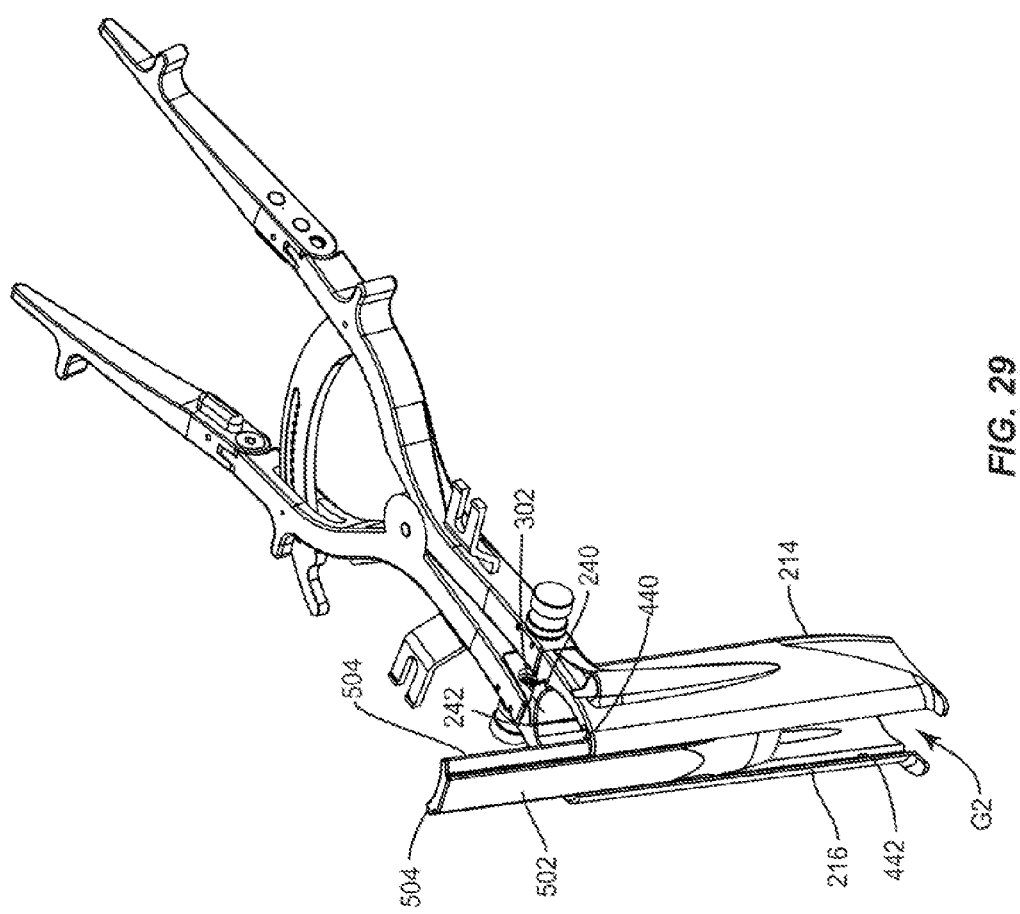
FIG. 29 is a perspective view of components of the system shown in FIG. 28.

Blade 502 is oriented for alignment with blades 214, 216 and grooves 440, 442, as shown in FIG. 28. Mating elements, such as, for example, flanges 504, disposed on sides of blade 502, are oriented for alignment with grooves 440, 442. Flanges 504 are manipulated for slidable engagement with surfaces 218, 230 such that blade 502 axially translates relative to blades 214, 216 for assembly with retractor 12, as shown in FIG. 29.

Figure 30:
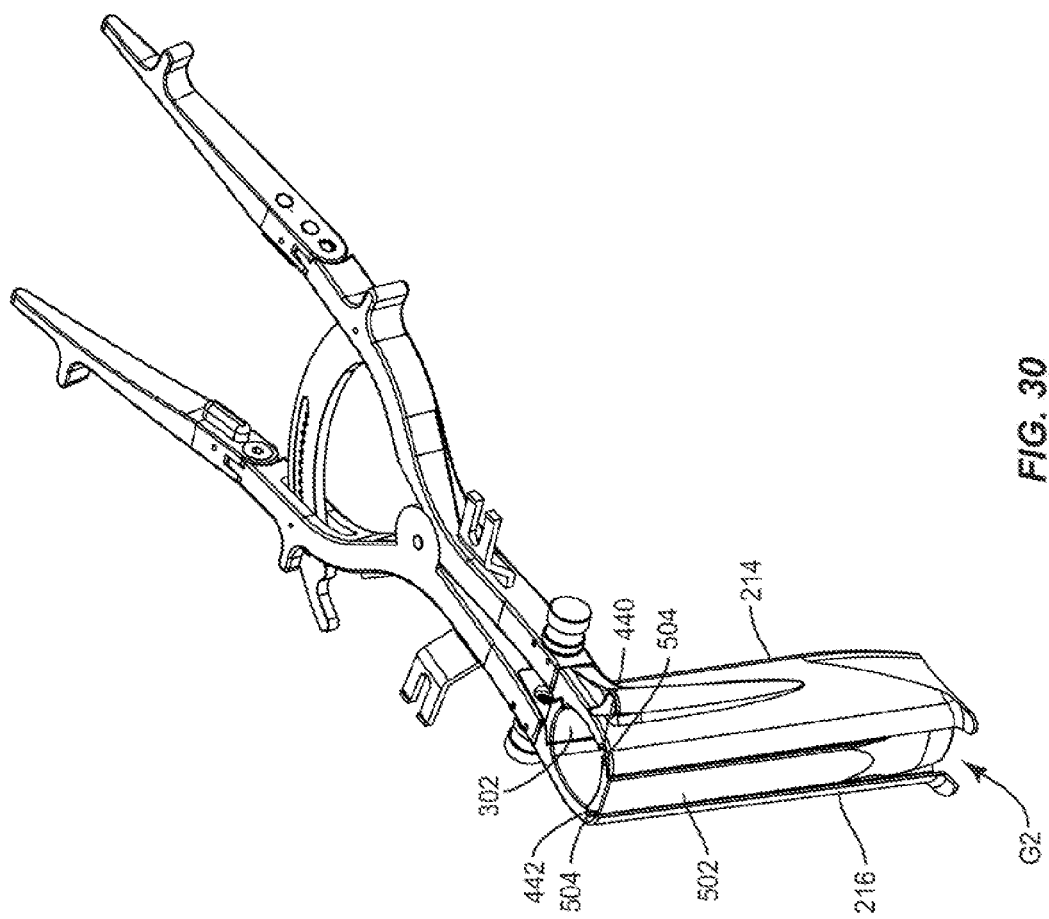
FIG. 30 is a perspective view of components of the system shown in FIG. 28.
Figure 31:
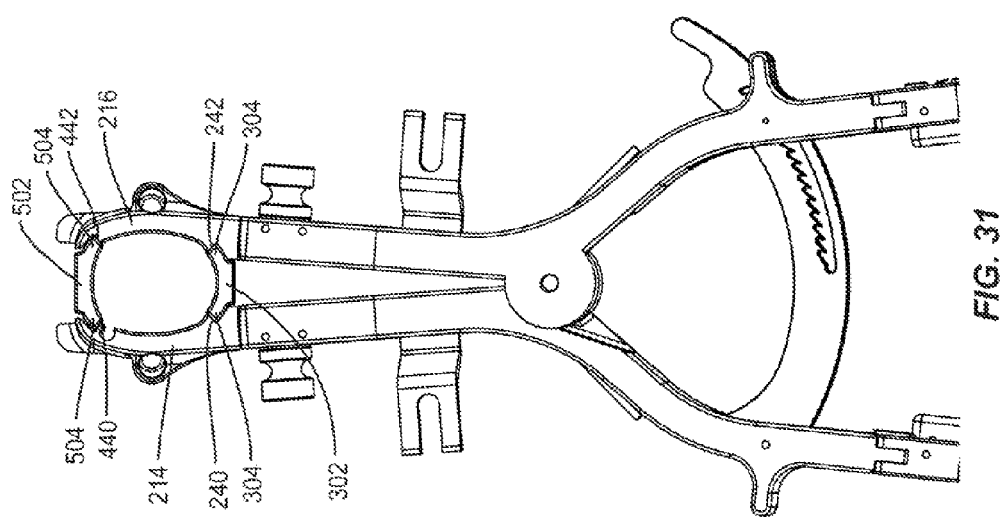
FIG. 31 is a break away plan view of components of the system shown in FIG. 28.

Blade 502 is selectively translated relative to blades 214, 216 and in an interlocking configuration with grooves 440, 442 to partially close and/or fully close a gap G2 of blades 214, 216. In some embodiments, blade 502 is adjustable to partially close gap G2, as shown in FIG. 29. In some embodiments, blade 502 is disposed in alignment with the ends of blades 214, 216 to fully close gap G2, as shown in FIG. 30. In some embodiments, disposal of blade 502 with blades 214, 216 partially encloses a surgical pathway, as described for example, in connection with use of retractor 12 herein. In some embodiments, disposal of blades 302, 502 with blades 214, 216, as described herein, fully encloses a surgical pathway. In some embodiments, blade 502 may be disposed with blades 214, 216, as described herein, in various surgical approaches to the spine, including anterior, posterior, posterior mid-line, direct lateral, postero-lateral, and/or antero-lateral approaches, and in other body regions, to partially close or fully close gap G2 and/or partially or fully enclose a surgical pathway.

In some embodiments, grooves 240, 242 are disposed adjacent to an anterior portion of blades 214, 216 and grooves 440, 442 are disposed adjacent to a posterior portion of blades 214, 216 relative to an orientation of retractor 12 with a surgical site and/or vertebrae, see, for example, that shown with regard to FIGS. 20 and 21. This configuration orients blade 302 with blades 214, 216 to close an anterior gap and/or opening, such as, for example, gap G1 between blades 214, 216 and orients blade 502 with blades 214, 216 to close a posterior gap and/or opening, such as, for example, gap G2 between blades 214, 216. In some embodiments, this orientation of blades 302, 502 with blades 214, 216 forms a completely enclosed tube of retractor 12 to fully enclose a surgical pathway. In some embodiments, groove 440 and/or groove 442 may be variously disposed with blades 214, 216. In some embodiments, blade 502 may be variously configured and dimensioned to accommodate variously configured and dimensioned retractor gaps and/or openings. In some embodiments, the mating elements may include key and slot elements, clips, latches, friction fit elements, pressure fit elements and/or adhesive elements.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
 a first member having a first handle portion and a first blade coupled to the first handle portion, the first blade comprising an inner surface and an outer surface;
 a second member having a second handle portion and a second blade coupled to the second handle portion, the second blade being disposed at an angle relative to the first blade, the second blade comprising an inner surface and an outer surface, at least one of the inner surfaces defining at least one mating element and the outer surfaces being engageable with tissue;
 a pin extending through the handle portions such that the first handle portion is pivotable relative to the second handle portion about the pin and the blades are relatively movable between a first configuration and a second configuration to space the tissue and define an opening between the blades, wherein the angle increases as the blades move from the first configuration to the second configuration; and
 at least one third member defining at least one mating element engageable with the at least one mating element of the inner surface such that the at least one third member is disposed within the opening.

2. A surgical instrument as recited in claim 1, wherein the at least one mating element of the inner surface comprises a longitudinal groove.

3. A surgical instrument as recited in claim 2, wherein the longitudinal groove comprises a uniformly configured channel.

4. A surgical instrument as recited in claim 2, wherein the longitudinal groove is disposed in a substantially co-axial or parallel alignment with a longitudinal axis of the first blade or the second blade.

5. A surgical instrument as recited in claim 1, wherein the inner surface of the first blade includes a first mating element and the inner surface of the second blade includes a second mating element.

6. A surgical instrument as recited in claim 5, wherein the first mating element comprises a longitudinal groove disposed in a substantially co-axial or parallel alignment with a longitudinal axis of the first blade and the second mating element comprises a longitudinal groove disposed in a substantially co-axial or parallel alignment with a longitudinal axis of the second blade.

7. A surgical instrument as recited in claim 1, wherein the at least one mating element of the at least one third member comprises a flange.

8. A surgical instrument as recited in claim 1, wherein the at least one mating element of the at least one third member is separately attachable with the at least one mating element of the inner surface in an interlocking configuration.

9. A surgical instrument as recited in claim 1, wherein the at least one mating element of the at least one third member is interlocked with the at least one mating element of the inner surface in a dovetail connection.

10. A surgical instrument as recited in claim 1, wherein the at least one third member is selectively disposed within the opening to at least partially close the opening.

11. A surgical instrument as recited in claim 1, wherein the at least one third member is disposed within the opening to fully close the opening.

12. A surgical instrument as recited in claim 11, wherein the opening comprises an anterior gap.

13. A surgical instrument as recited in claim 1, wherein the opening comprises an anterior gap and a posterior gap spaced from the anterior gap.

14. A surgical instrument as recited in claim 1, wherein the inner surface of the first blade comprises a pin hole to stabilize the surgical instrument with vertebrae.

15. A surgical instrument as recited in claim 1, further comprising a ratchet having a first end that is fixed to the first handle portion and a second end that extends through an aperture in the second handle portion, the ratchet including a plurality of teeth engageable with a locking pin of the second handle portion such that the blades are selectively and/or incrementally adjustable to a selected configuration.

16. A surgical instrument comprising:
a first member having a first handle portion and a first blade coupled to the first handle portion, the first blade comprising an inner surface defining a longitudinal groove and an outer surface;
a second member having a second handle portion and a second blade coupled to the second handle portion, the second blade being disposed at an angle relative to the first blade, the second blade comprising an inner surface defining a longitudinal groove and an outer surface, the outer surfaces being engageable with tissue;
a pin extending through the handle portions such that the first handle portion is pivotable relative to the second handle portion about the pin and the blades are relatively movable between a first configuration and a second configuration to space the tissue and define an opening between the members, wherein the angle increases as the blades move from the first configuration to the second configuration such that distal ends of the blades are be spaced apart from one another more than proximal ends of the blades when the blades are in the second configuration; and
a third member comprising flanges being axially translatable within the grooves such that the third member is disposed within the opening.

17. A surgical instrument as recited in claim 16, wherein the opening comprises an anterior gap and/or a posterior gap.

18. A surgical instrument as recited in claim 16, wherein the third member is disposed with the first blade and the second blade to at least partially enclose a surgical pathway.

19. A surgical instrument comprising:
a first member having an inner surface and an outer surface;
a second member having an inner surface and an outer surface, the second member being disposed at an angle relative to the first member, at least one of the inner surfaces defining at least one mating element and the outer surfaces being engageable with tissue, the members being relatively movable between a first configuration and a second configuration to space the tissue and define an opening between the members, wherein the angle increases as the members move from the first configuration to the second configuration; and
at least one third member defining at least one mating element that is removably engageable with the at least one mating element of the inner surface, the surgical instrument being movable between a first orientation in which the at least one third member is spaced apart from the first and second members and the first member engages the second member and a second orientation in which the at least one third member is disposed within the opening to space the first member apart from the second member,
wherein the inner surface of the first blade includes a first mating element comprising a longitudinal groove disposed in a substantially co-axial or parallel alignment with a longitudinal axis of the first blade and the inner surface of the second blade includes a second mating element comprising a longitudinal groove disposed in a substantially co-axial or parallel alignment with a longitudinal axis of the second blade.

20. A surgical instrument as recited in claim 19, wherein the at least one mating element of the at least one third member comprises a first flange configured for disposal in the longitudinal groove of the first mating element and a second flange configured for disposal in the longitudinal groove of the second mating element, the flanges each being disposed in a substantially co-axial or parallel alignment with a longitudinal axis of the at least one third member.

* * * * *

UNITED STATES PATENT AND TRADEMARK OFFICE
CERTIFICATE OF CORRECTION

PATENT NO. : 9,549,723 B2
APPLICATION NO. : 14/219821
DATED : January 24, 2017
INVENTOR(S) : Hynes et al.

It is certified that error appears in the above-identified patent and that said Letters Patent is hereby corrected as shown below:

In the Drawings

In Fig. 16, Sheet 12 of 26, delete "X1. X2, X4" and insert -- X1, X2, X4 --, therefor.

In the Specification

In Column 1, Line 15, delete "spondyolistheses," and insert -- spondylolisthesis, --, therefor.

In Column 1, Line 25, delete "discetomy," and insert -- discectomy, --, therefor.

In Column 2, Line 43, delete "away" and insert -- away, --, therefor.

In Column 2, Line 52, delete "away" and insert -- away, --, therefor.

In Column 2, Line 61, delete "away" and insert -- away, --, therefor.

In Column 3, Line 53, delete "instrument" and insert -- instrument, --, therefor.

In Column 4, Line 66, delete "practitioners" and insert -- practitioner's --, therefor.

In Column 7, Line 12, delete "potyetheretherketone" and insert -- polyetheretherketone --, therefor.

In Column 7, Line 30, delete "corraline" and insert -- coralline --, therefor.

In Column 7, Line 33, delete "polyglycoide," and insert -- polyglycolide, --, therefor.

In Column 10, Line 65, delete "example" and insert -- example, --, therefor.

In Column 13, Line 45, delete "to" and insert -- to, --, therefor.

Signed and Sealed this
Eleventh Day of April, 2017

Michelle K. Lee
*Director of the United States Patent and Trademark Office*

CERTIFICATE OF CORRECTION (continued)
U.S. Pat. No. 9,549,723 B2

In the Claims

In Column 17, Line 46, in Claim 16, delete "are be" and insert -- are --, therefor.